(12) United States Patent
Makriyannis et al.

(10) Patent No.: US 7,057,076 B2
(45) Date of Patent: Jun. 6, 2006

(54) BICYCLIC AND TRICYCLIC CANNABINOIDS

(75) Inventors: Alexandros Makriyannis, Mystic, CT (US); Spyridon P Nikas, Stamford, CT (US); Atmaram D Khanolkar, Coventry, RI (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 10/483,482

(22) PCT Filed: Jul. 11, 2002

(86) PCT No.: PCT/US01/21961

§ 371 (c)(1),
(2), (4) Date: Jul. 12, 2004

(87) PCT Pub. No.: WO03/005960

PCT Pub. Date: Jan. 23, 2003

(65) Prior Publication Data

US 2004/0236116 A1 Nov. 25, 2004

Related U.S. Application Data

(60) Provisional application No. 60/305,228, filed on Jul. 13, 2001.

(51) Int. Cl.
*C07C 49/115* (2006.01)
*C07C 49/23* (2006.01)
*C07D 311/78* (2006.01)
*A61K 31/35* (2006.01)

(52) U.S. Cl. .................. 568/326; 568/330; 549/280; 514/453

(58) Field of Classification Search ............. 568/326, 568/330; 549/280; 514/453
See application file for complete search history.

(56) References Cited

U.S. PATENT DOCUMENTS

| | | | |
|---|---|---|---|
| 3,041,343 A | 6/1962 | Jucker et al. |
| 3,465,024 A | 9/1969 | Brownstein et al. |
| 3,573,327 A | 3/1971 | Miyano |
| 3,577,458 A | 5/1971 | Brownstein et al. |
| 3,656,906 A | 4/1972 | Bullock |
| 3,838,131 A | 9/1974 | Gauthier |
| 3,886,184 A | 5/1975 | Matsumoto et al. |
| 3,897,306 A | 7/1975 | Vidic |
| 3,915,996 A | 10/1975 | Wright |
| 3,928,598 A | 12/1975 | Archer |
| 3,944,673 A | 3/1976 | Archer |
| 3,953,603 A | 4/1976 | Archer |
| 4,036,857 A | 7/1977 | Razdan et al. |
| 4,054,582 A | 10/1977 | Blanchard et al. |
| 4,087,545 A | 5/1978 | Archer et al. |
| 4,087,546 A | 5/1978 | Archer et al. |
| 4,087,547 A | 5/1978 | Archer et al. |
| 4,088,777 A | 5/1978 | Archer et al. |
| 4,102,902 A | 7/1978 | Archer et al. |
| 4,152,450 A | 5/1979 | Day et al. |
| 4,171,315 A | 10/1979 | Ryan |
| 4,176,233 A | 11/1979 | Archer et al. |
| 4,179,517 A | 12/1979 | Mechoulam |
| 4,188,495 A | 2/1980 | Althuis et al. |
| 4,208,351 A | 6/1980 | Archer et al. |
| 4,278,603 A | 7/1981 | Thakkar et al. |
| 4,282,248 A | 8/1981 | Mechoulam et al. |
| 4,382,943 A | 5/1983 | Winter et al. |
| 4,395,560 A | 7/1983 | Ryan |
| 4,497,827 A | 2/1985 | Nelson |
| 4,550,214 A | 10/1985 | Mehta |

(Continued)

FOREIGN PATENT DOCUMENTS

| | | |
|---|---|---|
| EP | 0276732 | 8/1988 |
| EP | 0444451 | 9/1991 |
| EP | 0471609 | 6/1993 |
| EP | 0737671 | 10/1996 |
| EP | 0860168 | 9/2001 |
| FR | 2240003 | 5/1975 |
| FR | 2735774 | 1/2000 |
| GB | 2027021 A | 2/1980 |
| JP | 57098228 | 6/1982 |
| JP | 2304080 | 12/1990 |
| WO | WO 97/00860 | 1/1997 |
| WO | WO 99/57106 | 11/1999 |
| WO | WO 99/57107 | 11/1999 |
| WO | WO 99/64389 | 12/1999 |
| WO | WO 00/32200 | 6/2000 |
| WO | WO 01/28329 | 4/2001 |
| WO | WO 01/28497 | 4/2001 |
| WO | WO 01/28498 | 4/2001 |
| WO | WO 01/28557 | 4/2001 |
| WO | WO 01/29007 | 4/2001 |
| WO | WO 01/32169 | 5/2001 |
| WO | WO 01/58869 | 8/2001 |
| WO | WO 02/058636 | 8/2002 |
| WO | WO 03/020217 | 3/2003 |
| WO | WO 03/035005 | 5/2003 |
| WO | WO 03/063758 | 8/2003 |
| WO | WO 03/064359 | 8/2003 |

OTHER PUBLICATIONS

Supplementary Partial European Search Report for EPO application No. EP 02 74 9947 dated May 4, 2005.
U.S. Appl. No. 09/600786, filed Nov. 24, 1999, Makriyannis et al (copy not included, this is the U.S. National Phase of the Int'l Application published as WO 00/32200 enclosed herewith).

(Continued)

*Primary Examiner*—Sikarl A. Witherspoon
(74) *Attorney, Agent, or Firm*—Alix, Yale & Ristas, LLP

(57) ABSTRACT

Novel bicyclic-cannabinoids and hexahydrocannabinol analogs are presented. These compounds, when administered in a therapeutically effective amount to an individual or animal, results in a sufficiently high level of that compound in the individual or animal to cause a physiological response. The physiological response useful to treat a number of physiological conditions.

16 Claims, No Drawings

U.S. PATENT DOCUMENTS

| | | |
|---|---|---|
| 4,758,597 A | 7/1988 | Martin et al. |
| 4,812,457 A | 3/1989 | Narumiya |
| 4,876,276 A | 10/1989 | Mechoulam |
| 4,885,295 A | 12/1989 | Bell et al. |
| 5,053,548 A | 10/1991 | Tanaka et al. |
| 5,068,234 A | 11/1991 | D'Ambra et al. |
| 5,147,876 A | 9/1992 | Mizuchi et al. |
| 5,223,510 A | 6/1993 | Gubin et al. |
| 5,284,867 A | 2/1994 | Kloog |
| 5,324,737 A | 6/1994 | D'Ambra et al. |
| 5,434,295 A | 7/1995 | Mechoulam et al. |
| 5,440,052 A | 8/1995 | Makriyannis et al. |
| 5,462,960 A | 10/1995 | Barth et al. |
| 5,489,580 A | 2/1996 | Makriyannis et al. |
| 5,521,215 A | 5/1996 | Mechoulam |
| 5,532,237 A | 7/1996 | Gallant et al. |
| 5,538,993 A | 7/1996 | Mechoulam |
| 5,576,436 A | 11/1996 | McCabe et al. |
| 5,605,906 A | 2/1997 | Lau |
| 5,607,933 A | 3/1997 | D'Ambra et al. |
| 5,618,955 A | 4/1997 | Mechoulam et al. |
| 5,624,941 A | 4/1997 | Barth et al. |
| 5,635,530 A | 6/1997 | Mechoulam |
| 5,688,825 A | 11/1997 | Makriyannis et al. |
| 5,744,459 A | 4/1998 | Makriyannis et al. |
| 5,747,524 A | 5/1998 | Cullinan et al. |
| 5,804,601 A | 9/1998 | Kato et al. |
| 5,817,651 A | 10/1998 | D'Ambra et al. |
| 5,872,148 A | 2/1999 | Makriyannis et al. |
| 5,874,459 A | 2/1999 | Makriyannis et al. |
| 5,925,628 A | 7/1999 | Lee et al. |
| 5,925,768 A | 7/1999 | Barth et al. |
| 5,932,610 A | 8/1999 | Shohami et al. |
| 5,948,777 A | 9/1999 | Bender et al. |
| 6,013,648 A | 1/2000 | Rinaldi et al. |
| 6,028,084 A | 2/2000 | Barth et al. |
| 6,096,740 A | 8/2000 | Mechoulam |
| 6,127,399 A | 10/2000 | Yuan |
| 6,166,066 A | 12/2000 | Makriyannis et al. |
| 6,284,788 B1 | 9/2001 | Mittendorf et al. |
| 6,391,909 B1 | 5/2002 | Makriyannis et al. |
| 6,579,900 B1 | 6/2003 | Makriyannis et al. |
| 6,610,737 B1 | 8/2003 | Garzon et al. |
| 2002/0119972 A1 | 8/2002 | Leftheris et al. |
| 2002/0173528 A1 | 11/2002 | Fride et al. |
| 2003/0120094 A1 | 6/2003 | Makriyannis et al. |
| 2003/0149082 A1 | 8/2003 | Makriyanis et al. |
| 2004/0077649 A1 | 4/2004 | Makriyanis et al. |
| 2004/0077851 A1 | 4/2004 | Makriyanis et al. |
| 2004/0087590 A1 | 5/2004 | Makriyanis et al. |

OTHER PUBLICATIONS

U.S. Appl. No. 09/698,071, filed Oct. 30, 2000, *1* Fride et al, (copy not included, this is the parent application for US Publication No. 2002/0173528, enclosed herewith).

U.S. Appl. No. 09/701989, filed Jun. 9, 1999, Makriyannis et al (copy not included, this is the U.S. National Phase of the Int'l Application published as WO 99/64389 enclosed herewith).

U.S. Appl. No. 10/110865, filed Oct. 18, 2000, Makriyannis et al (copy not included, this is the U.S. National Phase of the Int'l Application published as WO 01/28497 enclosed herewith).

U.S. Appl. No. 10/110830, filed Oct. 18, 2000, Makriyannis et al (copy not included, this is the U.S. National Phase of the Int'l Application published as WO 01/28329 enclosed herewith).

U.S. Appl. No. 10/110812, filed Oct. 18, 2000, *1* Makriyannis et al (copy not included, this is the U.S. National Phase of the Int'l Application published as WO 01/28498 enclosed herewith).

U.S. Appl. No. 10/110862, filed Oct. 18, 2000, Makriyannis et al (copy not included, this is the U.S. National Phase of the Int'l Application published as WO 01/29007 enclosed herewith).

U.S. Appl. No. 10/111059, filed Oct. 18, 2000, Makriyannis et al (copy not included, this is the U.S. National Phase of the Int'l Application published as WO 01/28557 enclosed herewith).

U.S. Appl. No. 10/483482, filed Jul. 11, 2002, Makriyannis et al (copy not included, this is the U.S. National Phase of the Int'l Application published as WO 03/005960 enclosed herewith).

U.S. Appl. No. 10/493093, filed Oct. 28, 2002, Makriyannis et al (copy not included, this is the U.S. National Phase of the Int'l Application published as WO 03/35005 enclosed herewith).

U.S. Appl. No. 10/647544, filed Aug. 25, 2003, Makriyannis et al.

U.S. Appl. No. 10/790498, filed Mar. 1, 2004, Makriyannis et al.

Abadji V., Lin S., Taha G., Griffin G., Stevenson L.A., Pertwee R.G., Makriyannis A.; "(R)–Methanandamide: a chiral novel anandamide possessing higher potency and metabolic stability"; J. Med. Chem.; 37(12); 1889–1893; 1994; Coden: JMCMAR; ISSN: 0022–2623; XP002040932.

*1* Alo, B.I.; Kandil, A.; Patil, P. A.; Sharp, M. J.; Siddiqui, M. A.; and Snieckus, V. Sequential Directed Ortho Metalation–Boronic Acid Cross–Coupling Reactions. A general Regiospecific Route to Oxygenerated Dibenzo[b,d] pyran–6–ones Related to Ellagic Acid, J. Org. Chem. 1991, 56, 3763–3768.

*1* *** Archer et al; "cannabinoids, synthesis approaches to 9–ketocannabinoids."; J. Org. Chem.; vol. 42; No. 13; 2277–2284; (1977).

Arnone M., Maruani J., Chaperone P, et al, Selective inhibition of sucrose and ethanol intake by SR141716, an antagonist of central cannabinoid (CB1) receptors, Psychopharmacal, (1997) 132, 104–106. (abstract only).

Barnett–Norris et al; "Exploration of biologically relevant conformations of anandamide, . . . "; J. Med. Chem.; vol. 41; 4861–4872; 1998.

*1* Beak, P.; and Brown, R.A., The Tertiary Amide as an Effective Director of Ortho Lithiation, J. Org. Chem. 1982, 47, 34–36.

Belgaonkar et al.; "synthesius of isocoumarins"; Indian J. Chem; vol. 13; No. 4; 336–338, 1975 (abstract only).

*1* Beltramo M., Stella N., Calignano A., Lin S. Y., Makriyannis A., Piomelli D; "Functional Role Of High–Affinity Anandamide Transport, as Revealed By Selective Inhibition"; Science, vol. 277; 1094–1097; 1997.

Beltramo M., Stella M., Calignano A., Lin S. Y., Makriyannis A., Piomelli D; "Identification and Functional Role of High Affinity Anandamide Transport"; The Neurosciences Institute (1 page).

*1* Berdyshev EV, Cannabinoid receptors and the regulation of immune response. Chem Phys Lipids. Nov. 2000; 108(1–2):169–90.

Berglund et al; "Structural requirements for arachidonylethanolamide interaction with CB1 and CB2 cannabinoid receptors: . . . "; Prostanglandins, leukotrienes ands essential fatty acids; 59(2); 111–118; (1998). (abstract only).

Bodnar, V.N., Lozinskii, M.O., Pel'kis, P.S.; "Synthesis fo 2,5–disubstituted 1,3,4–oxadiazoles and 1,4–dihydro–1,2,4, 5–tetrazines"; Ukrainskii Khimicheskii Zhurnal (Russian Edition); 48(12); 1308–1311; 1982 (abstract only).

*1* Bracey, M et al, Structural Adaptations in a Membrane Enzyme That Terminates Endocannabinoid Signaling. Science 2002; 298 (5599): 1793–1796.

Brenneisen R, Pgli A, Elsohly MA, Henn V. Spiess Y: That effect of orally and rectally administered Δ9—tetrahydrocannabinol on spasticity, a pilot study with 2 patients. Int. J. Clin Pharmacol Ther. (1996) 34:446–452. (abstract only).

*** Brotchie JM: *Adjuncts to dopamine replacement a pragmatic approach to reducing the problem of dyskinesia in Parkinson's disease. Mov. Disord.* (1998)13:871–876.

Brown et al; "Synthesis and hydroboration of (−)–2–phenylapopinene, Comparison of mono(2–phenylapoisopinocampheyl)borane with its 2–methyl and 2–ethyl analogues for the chiral hydroboration of representative alkenes"; J. Org. Chem.; 55(4); 1217–1223; (1990).

Buckley NE, McCoy KI, Mpzey E et al, "Immunomodulation by cannabinoids is absent in mice deficient for the cannabinoid CB2 receptor"; Eur. J Pharmacol (2000) 396:141–149.

Burstein et al; "detection of cannabinoid receptors . . . "; Biochem. Biophys. Res. Commun.; vol. 176(1); 492–497; 1991 (abstract only).

*1* Busch–Peterson et al; "Unsaturated side chain beta–11–hydroxyhexahydrocannabinol analogs"; J. Med. Chem.; 39; 3790–3796; (1996).

Calignano A, La Rana G. Diuffrida A, Piomelli D.; "Control of pain initiation by endogenous cannabinoids"; Nature (1998) 394:277–291. (abstract only).

Calignano A., La Rana G., Beltramo, M., Makriyannis A., Piomelli D.; "Potentiation of Anandamide Hypotension by the Transport Zinhibitor, AM404", Eur. J. Pharmacol.; 1997; 337 R1–R2.

Calignano A., La Rana G., Makriyannis A., Lin. S., Beltramo M., Piomelli D; "Inhibition of Intestinal Motility by Anandamide, an Endogenous Cannabinoid"; Eur. J. Pharmacol.; 1997; 340 R7–R8.

*1* Campbell FA et al; "Are cannabinoids an effective and safe treatment option in the management of pain? A qualitative systematic review"; BMJ. Jul. 7, 2001;323(7303):13–6.

*1* Charalambous A. et al; "5'–azido Δ8–THC: A Novel Photoaffinity Label for the Cannabinoid Receptor"; J. Med. Chem., 35, 3076–3079 (1992).

Charalambous A. et al; "Pharmacological evaluation of halogenated . . . "; Pharmacol. Biochem. Rehav.; vol. 40; No. 3; 509–512; 1991.

*1* Cheng et al; "Relationship Between the Inhibition Constant (Ki) and the concentration of Inhibitor which causes 50% Inhibition (IC50) of an Enzymatic Reaction"; Biochem. Pharmacol., 22, 3099–3102, (1973) (abstract only).

Cherest M., Luscindi X.; "The action of acetyl chloride and of acetic anhydride on the lithium nitronate salt of 2–phenylnitroethane . . . "; Tetrahedron; 42(14); 3825–3840; 1986; in French with English abstract.

Cherest M., Lusinchi X.; "A novel electrophilic N–amidation via electron deficient complexes: action of ferric chloride on N–acetyloxyamides"; Tetrahedron Letters; 30(6); 715–718; 1989.

Colombo G, Agabio R, Diaz G. et al; "Appetite suppression and weight loss after the cannabinoid antagonist SR141716"; Life Sci. (1998) 63–PL13–PL117. (abstract only).

*** Compton D.R. et al; *J. Pharmacol. Exp. Ther.*; 260; 201–209; 1992.

Compton et al; "Synthesis and pharmacological evaluation of ether and related analogues of delta8–. delta9– and delta9,11–tetrahydrocannabinol"; J. Med. Chem; vol. 34; No. 11; 3310–3316; 1991.

Consroe P, Musty R, Rein J, Tillery W, Pertwee R; "The perceived effects of smoked cannabis on patents with multiple sclerosis"; Eur. Neurol. (1997) 38–44–48. (abstract only).

*1* Coxon et al; "Derivatives of nopinone"; Aust. J. Chem.; 23; 1069–1071; (1970) (abstract only).

Crawley et al; "Anandamide, an endogeneous ligand of the cannabinoid receptor, induced hypomotility and hypothermia in vivo in rodents"; Pharmacology Biochemistry and Behavior; vol. 46, 967–972; 1993.

D'Ambra et al; "C–attached aminoalkylindoles: potent cannbinoid mimetics"; Bioorg. & Med. Chem. Lett., 1996, 6(1), 17–22.

*** D'Amour F.E., Smith D.L.; *J. Pharmacol. Exp. Ther.*; 72; 74–79; 1941.

Demuynck L. et al; "Rearrangement of Indolo[2,3–a]quinolizidines to derivatives with E–azaaspidospermane skeleton"; Tetrahedron Letters; 30(6) 710–722; 1989; in French with English abstract.

DePetrocellis L, Melck D, Palmisano A. et al; "The endogeneous cannabinoid anandamide inhibits human breast cancer cell proliferation"; Proc. Natl. Acad. Sci. USA (Jul. 1998) 95:8375–8380.

Desarnaud F., Cadas H., Piomelli D.; "Anandamide amidohydrolase activity in rat brain microsomes"; J. Biol. Chem.; 270; 6030–6035; (1995).

Deutsch D.G. et al; "Fatty acid sulfonyl fluorides inhibit anandamide metabolism and bind to cannabinoid receptor"; Biochem. Biophys. Res. Commun. 231(1); 217–221; 1997; CODEN: BBRCA9; ISSN:0006–291X; XP002040933.

Deutsch D.G., Chin S.A.; "Enzymatic synthesis and degradation of anandamide, a cannabinoid receptor agonist"; Biochemical Pharmacology; 46(5); 791–796; 1993.

*1* Devane, W.A. et al; "Determination and Characterization of a Cannabinoid Receptor in a Rat Brain"; Mol. Pharmacol., 34, 605–613 (1988).(abstract only).

Di Marzo, V., Melck, D., Bisogno, T., DePetrocellis, L.; "Endocannabinoids: endogenous cannabinoid receptor ligands with neuromodulatory action"; Trends Neurosci. (1998) 21:521–528.

*1* *** Dodd, R.P. et al, *A Rapid Method for Preparing Synaptosomes: Comparison with Alternative Procedures, Brain Res.*, 226, 107–118 (1981).

Dominiami et al; "Synthesis of 5–(tert–Alkyl)resorcinols"; J. Org. Chem. 42(2); 344–346; (1977).

*1* Drake et al, "classical/nonclassical hybrid cannabinoids"; J. Med. Chem.; vol. 41(19); 3596–3608 (1998).

*1* Edery et al; "Activity of novel aminocannabinoids in baboons"; J. Med. Chem.; 27; 1370–1373 (1984).

Eissenstat et al; "Aminoalkylindoles: structure–activity relationships of novel cannabinoid mimetics"; J. Med. Chem. 1995, vol. 38, No. 16, pp. 3094–3105; XP 000651090.

*1* Fahrenholtz, K. E., Lurie, M. and Kierstead, AR. W.; "The Total Synthesis of dl–Δ9–Tetrahydrocannabinol and Four of Its Isomers"; J. Amer. Chem. Soc. 1967, 89(23), 5934–5941.

Fahrenholtz; "The synthesis of 2 metabolites of (−)–delta eight–tetrahydrocannabinol"; J. Org. Chem.; vol. 37 (13); 1972; XP002111824.

Fisera, L., Kovac, J., Lesco, J., Smahovsky, V.; "Furan derivatives. Part CLVI. 1,3–dipolar cycloadditions of heterocycles. V. Reaction of C–acetyl–N–phenylnitrilimine with furan derivatives"; Chemicke Zvesti; 35(1); 93–104 1981 (abstract only).

Fride, E. & Mechoulam, R.; "Pharmacological activity of the cannabinoid receptor agonist, anandamide, a brain constituent"; European Journal of Pharmacology, vol. 231; 313–314; 1993.

*1* Galiegue S et al. ; "Expression of central and peripheral cannabinoid receptors in human immune tissues and leukocyte subpopulations"; Eur J Biochem.; Aug. 15, 1995;232(1):54–61. (abstract only).

*1* Gareau, Y.; Dufresne, C.; Gallant, M.; Rochette, C.; Sawyer, N.; Slipetz, D. M.; Tremblay, N.; Weech, P. K.; Metters, K. M.; Labelle, M.; "Structure activity relationships of tetrahydrocanabinol analogs on human cannabinoid receptors"; Bioorg. Med. Chem. Lett. 1996, 6(2), 189–194.

Gold et al; "A comparison of the discriminative stimulus properties of delta9–tetrahydrocannabinol and CP 55,940 in rats and rhesus monkeys"; J. Pharmacol. Exp. Ther.; vol. 262(2); 479–486; 1992.

*** Green K. *Marijuana smoking vs. cannabinoids for glaucoma therapy. Arch. Ophibalmol.* (1998) feb 433–1437.

Hampson, A.J., Grimaldi M. Axpirod J. Wink D; "Cannabidiol and (−) Δ9 tetrahydrocannabinol are neuroprotective antioxidants"; Proc. Natl Acad Sci. USA (Jul. 1998) 95; 8268–8273.

Hargreaves, K. et al; "A new sensitive method for measuring thermal nociception in cutaneous hyperalgesia"; Pain; 32; 77–88; (1988) (abstract only).

*** Hemming M, Yellowlees PM; "*Effective treatment of Tourette's syndrome with marijuana*"; *J. Psychopharmacol*, (1993) 7:389–391.

Herzberg U, Eliav E, Bennett GJ, Kopin IJ; "The analgesic effects of R(+) WIN 55,212–2 mesylate, a high affinity cannabinoid agonist in a rat model of neuropathic pain"; Neurosci. Letts. (1997) 221; 157–160.

Hillard, C. J., Edgemond, W. S., Jarrahian W., Campbell, W. B; "Accumulation of N–Arachidonoylethanolamine (Anandamide) into Cerebellar Granule Cells Occurs via Facilitated Diffusion"; Journal of Neurochemistry; 69; 631–638 (1997).

Horrovoets A.J.G et al; "Inactivation of escherichia coli outer membrane phospholipase A by the affinity label hexadecanesulfonyl fluoride"; Eur. J. Biochem.; 198; 247–253; 1991.

Horrevoets A.J.G et al.; "Inactivation of reconstituted escherichia coli outer membrane phospholipase A by membrane–perturbing peptides results in an increased reactivity towards the affinity label hexadecanesulfonyl fluoride"; Eur. J. Biochem.; 198; 255–261; 1991.

Howlett et al; "Azido and isothicyanato substituted aryl pyrazoles bind covalently to the CB1 cannabinoid receptor and impair signal transduction"; Journal of Neurochemistry; vol. 74(5) (2000) 2174–2181; XP001097394.

Howlett et al; "Stereochemical effects of 11–OH–delta 8 tetrahydrocannabinol–dimethylheptyl to inhibit adenylate cyclase and bind to the cannabinoid receptor"; Neuropharmacology; vol. 29(2); 161–165; 1990.

*1* Huffman et al; "3–(1',1'–deimethylbutyl)—deoxy–delta 8THC and related compounds: synthesis of selective ligands for the CB2 receptor"; Bioorganic and Medicinal Chemistry; vol. 7; 2905–2914; (1999).

*1* Huffman et al; "Stereoselective synthesis of the epimeric delta 7–tetrahydocannabinols"; tetrahedron; vol. 51(4); 1017–1032; (1995).

*1* Huffman et al; "Synthesis of 5',11 dihydroxy delta 8 tetrahydrocannabinol"; Tetrahedron, vol. 53(39), pp 13295–13306 (1997).

Huffman et al; "Synthesis of a tetracyclic, conformationally constrained analogue of delta8–THC"; Bioorganic & Medicinal Chemistry; vol. 6(12); 2281–2288; 1998; XP002123230.

*1* Huffman et al.; "Synthesis of both enantiomers of Nabilone from a common intermediate. Enantiodivergent synthesis of cannabinoids"; J. Org. Chem.; 1991, 56, 2081–2086.

*** Joy JE, Wagtson SJ, Benson JA; "*Marijuana and Medicine Assessing the Science Base*"; National Academy Press, Washington, DC, USA (1999).

*1* Kaminski NE; "Regulation of the cAMP cascade, gene expression and immune function by cannabinoid receptors"; J Neuroimmunol. Mar. 15, 1998;83(1–2);124–32.

Kawase M. et al; "Electrophilic aromatic substitution with N–methoxy–N–acylnitrenium ions generated from N–chloro–N–methoxyamides: synthesis of nitrogen heterocyclic compounds bearing a N–methoxyamide group"; J. Org. Chem.; 54; 3394–3403; 1989.

Khanolkar A., Abadji V., Lin S., Hill W., Taha G., Abouzid K., Meng Z., Fan P., Makriyannis A.; "Head group analogues of arachidonylethanolamide, the endogenous cannabinoid ligand", J. Med. Chem.; vol. 39(22); 4515–4519; (1996).

*1* Khanolkar et al; "Molecular probes for the cannabinoid receptors"; Chemistry and Physics of Lipids; 108; 37–52; (Jul. 18, 2000).

*1* Klein T.W. et al, "The cannabinoid system and cytokine network"; Proc Soc Exp Biol Med. Oct. 2000; 225(1):1–8; (abstract only).

*1* Klein TW et al, "Cannabinoid receptors and immunity"; Immunol Today; Aug. 1998; 19(8):373–81.

Koutek B. et al; "Inhibitors of arachidonyl ethanolamide hydrolysis"; J. Biol. Chem.; 269(37); 22937–40; 1994; CODEN: JBCHA3: ISSN: 0021–9258; XP002040931.

*1* Kumar RN, et al; "Pharmacological actions and therapeutic uses of cannabis and cannabinoids"; Anesthesia, 2001, 56: 1059–1068 (abstract only).

Lan, R et al; "Structure activity relationships of pyrazole derivatives as cannabinoid receptor antagonists"; J. Med. Chem.; vol. 42(4); 769–776; (1999).

*1* Lavalle et al; "Efficient conversion of (1R, 5R)–(+)–alpha–pinene to (1S, 5R)–(-)–nopinene"; J. Org. Chem.; vol. 51(8); 1362–1365; (1986).

Lin S., Khanolkar A., Fan P., Goutopolous A., Qin C., Papahadjis D., Makriyannis A.; "Novel Analogues of arachidonylethanolamide (anandamide): affinities for the CB1 and CB2 Cannabinoid Receptors and Metabolic Stability"; J. Med. Chem.; vol. 41; 5353; 1998.

*1* Loev, B., Bender, P. E., Dowalo, F., Macko, E., and Fowler, P.; "Cannabinoids. Structure–Activity Studies Related to 1,2–Dimethylheptyl Derivatives"; J. Med. Chem.; vol. 16(11); 1200–1206; 1973.

Lozinskii, M.O., Bodnar, V.N., Konovakikhin, S.V., D'yachenko, O.A., Atovmyan, L.O.; "Unusual transformations of arylhydrazonyl chlorides of oxalic acid ethyl ester"; Izvestiya Akademii Nauk SSSr, Seriya Khimicheskaya; 11; 2635–2637; 1990 (abstract only).

Ludt, R.E. et al; "A comparison of the synthetic utility of n–butyllithium and lithium diisopropylamide in the metalations of N,N–dialkylouamides"; J. Org. Chem.; 38(9); 1668–1674 (1983).

*1* *** Maccarron M., *Endocannabinoids and their actions. Vitamins and Hormones 2002*;65:225–255.

Mackie K., Devane W.A., Hille B.; "Anandamide, an endogenous cannabinoid, inhibits calcium currents as a partial agonist in N18 neuroblastoma cells"; Mol. Pharmacol; 44; 498–0503 (1993).

*** Markwell et al; *Anal. Biochem.*; 87:206 (1978).

Martin et al; "Behavioral, biochemical, and molecular modeling evaluations of cannabinoid analogs"; Pharmacol. Biochem. Behav.; vol. 40(3); 471–478; 1991.

Martyn CN. Illis LS, Thom J.; "Nabilone in the treatment of multiple sclerosis"; Lancet (1995) vol. 345; pp. 579.

Matsumoto et al; "Cannabinoids 1.1–amino–and 1 mercapto–7,8,9,10–tetrahydro–6h–dibenzo[b,d]pyrans"; J. of Med. Chem.; vol. 20(1); 17–24; 1977; XP00211825.

*** Maurer M, Henn V, Dittrich A, Hofmann A. *Delta–9–tetrahydrocannabinol shows antispastic and analgesic effects in a single case double–blind trial. Eur. Arch. Psychiat. Clin. Neurosci.* (1990), Z40:1–4.

Mavromoustakos, T. et al; "Studies on the thermotropic effects of cannabinoids on phosphatidylcholine bilayers using differential scanning calorimetry and small angle X–ray diffraction"; Biochimica et Biophysica Acta; vol. 1281(2); 1996; XP002111823.

*1* Mechoulam et al; "Stereochemical Requirements for cannabinoid activity"; J. Med. Chem.; 23(10); 1068–1072; (1980).

*1* Mechoulam et al; "Synthesis of the individual, pharmacologically distinct, enantiomers of a tetrahydrocannabinol derivative"; Tetrahedron Asymmetry; 1: 311–314; (1990) (abstract only).

*1* *** Mechoulam et al; *Tetrahedron Asymmetry*; 1: 315–318; (1990).

*** Mechoulam, *"Cannabinoids as therapeutic agents"*; CRC press, 1986.

Meltzer et al; "An improved synthesis of cannabinol and cannabiorcol"; Synthesis; 1981:985 (1981).

*1* *** Melvin et al; *drug design and discovery*; 13; 155–166 (1995).

*1* Melvin et al; "Structure–activity relationships for cannabinoid receptor–binding and analgesic activity: studies of bicyclic cannabinoid analogs"; Mol. Pharmacol.; 44(5); 108–1015 (1993).

Merck Index; 11th edition; "Tetrahydrocannabinols" compound No. 9142; 1989.

*** Morgan Dr: *Therapuetic Uses of Cannabis*. Harwood Academic Publishers, Amsterdam. (1997).

*1* *** Morris, S.; Mechoulam, R.; and Irene, Y., *Halogenation of phenols and Phenyl ethers with Potassium Halides in the Presence of 18–Crown–6 on Oxidation with m–Chloroperbenzoic Acid, J. Chem. Soc.*, Perkin Trans. 1 1987, 1423–1427.

*** Muller–Vahl KB, Kolbe H, Schneider U, Emrich, *HM Cannabis in movement disorders. Porsch. Kompicmentarmed (1999) 6 (suppl. 3) 23–27.*

*** Muller–Vahl KB, Schneider U, Kolbe H, Emrich, HM. *Treatment of Tourette's syndrome with delta–9–tetrahydrocannabinol. Am. J. Psychiat.* (1999) 156–195.

*1* *** Nahas G, *Marijuana and Medicine*; 1999, Human Press Inc., Totowa, NJ.

Neunhoeffer O., Gottschlich R.; "Acylating activity of O–acylated hydroxylamine derivatives"; Justus Liebigs Ann. Chem.; 736; 100–109; 1970; in German with English abstract.

Novak, J et al; Cannabis, part 27, synthesis of 8–, 10– and 11–oxygenated cannabinoids; J. Chem. Soc. Perkin Trans.; 2867–2871; (1983) (abstract only).

Nye et al; "High affinity cannabinoid binding sites in brain membranes labelled with [H]–5'–trimethylammonium delta8–tetrahydrocannabinol"; J. Pharmacol. Exp. Ther.; vol. 234(3); 784–791; 1985.

Pacheco M, et al; "Aminoalkylindoles: Actions On Specific G–Protein–Linked Receptors"; J. Pharmacol. Exp. Ther.; vol. 257, No. 1, pp. 170–183 and 172 Table (1991).

*1* *** Palmer et al; *current pharmaceutical design*; 6; 1381–1397; (2000).

*1* Papahatjis et al; "A new ring–forming methodology for the synthesis of conformationally constrained bioactive molecules"; Chemistry Letters, 192; (2001).

*1* Papahatjis et al; "Pharmacophoric requirements for cannabinoid side chains: multiple bond and C1'–substituted delta8–tetrahydrocannabinols"; J. Med. Chem.; 41(7); 1195–1200; (1998).

Pertwee et al; "AM630, a competitive cannabinoid receptor agonist"; Life Sci 1995, 56(23/24), 1949–1955; XP 000653566.

Pertwee et al; "Pharmacological characterization of three novel cannabinoid receptor agonists in the mouse isolated vas deferens"; Eur. J. Pharmacol. 1995, 284, 241–247; XP–001041044.

*** Pertwee et al; *Br. J. Pharmacol.*; 105; 980 1992.

*1* Pertwee; Pharmacology of cannabinoid CB1 and CB2 receptors; Pharmacol. Ther., vol. 74(2); pp129–180; (1997); XP002226467.

Petrov, M.L., Terent'eva, N.A., Potekhin, K.A., Struchkov, Yu. T.; ".alpha.,.beta.–unsaturated thiolates and their analogs in cycloaddition reactions. XVIII. Reaction of (2–phenylethynyl)tellurolates with C–ethoxycarbonyl–N–Phenylnitrilimine"; Zhurnal Organicheskoi Khimii; 29(7); 1372–1378; (1993) (abstract only).

\*\*\* Pinnegan–Ling D, Musty R.; *Marinol and phantom limb pain: a case study. Proc Inv. Cannabinoid Rea. Sec.* (1994):53.

Piomelli D., Beltramo M., Glasnapp S., Lin S.Y., Goutopoulos A., Xiw X–Q., Makriyannis A.; "Structural determinants for recognition and translocation by the anandamide transporter"; Proc. Natl. Acad. Sci. USA; 96; 5802–5807; (1999).

Pitt et al; "The synthesis of Deuterium, carbon–14 and carrier free tritium labelled cannabinoids"; Journal of Labelled Compounds; vol. 11(4); 551–575; 1975: XP002123229.

\*\*\* Porreca F., Mosberg H.I., Hurst R., Hruby V.J., Burks T.F.; *"Roles of mu, delta and kappa opiod receptors in spinal and supraspinal mediation of gastrointestinal transit effects and hot–plate analgesia in the mouse"; J. Pharmacol. Exp. Ther.*; 230; 341–348; (1994).

Razdan et al; "Drugs derived from cannabinoids. 6. .Synthesis of cyclic analogues of dimethylheptylpyran"; J. Med. Chem.; vol. 19(5); 719–721; 1976 (abstract only).

Reggio et al; "Characterization of a region of steric interference at the cannabinoid receptor using the active analog approach"; J. Med. Chem. United States; vol. 36(12); 1761–1771; 1993.

\*1\* Rhee, M. H.; Vogel, Z.; Barg, J.; Bayewitch, M.; Levy, R.; Hanus, L.; Breuer, A.; and Mechoulam, R.; "Cannabinol Derivatives: Binding to Cannabinoid Receptors and Inhibition of Adenylcyclase"; J. Med. Chem. 1997, 40(20); 3228–3233.

\*1\* \*\*\* Rice AS. *Cannabinoids and pain. Curr Opin Investig Drugs*. Mar. 2001;2(3):399–414.

Richardson JD, Aanonsen I, Hargreaves KM; "Antihyperalgesic effects of a spinal cannabinoids"; Eur. J. Pharmacol. (1998) 346:145–153.

Richardson JD, Kilo S. Hargreaves KM; "Cannabinoids reduce dryperalgesia and inflammation via interaction with peripheral CB1 receptors"; Pain (1998) 75:111–119.

Rinaldi–Carmona et al; "Biochemical and pharmacological characterization of SR141716A, the first potent and selective brain cannabinoid receptor antagonist"; Life Sci.; vol. 56(23/24); 1941–1947 (1995).

Rinaldi–Carmona et al; "SR141716A, a potent and selective antagonist of the brain cannabinoid receptor"; FEBS Lett.; 350; 240–244; (1994).

Rompp Chemie Lexikon; Falbe and Regitz; "band 1–A–C1, 8"; Aufl, Thieme Verlag; Stuttgart, S 569–570; 1989.

Santus, Maria; "Studies on thioamides and their derivatives. IX. Synthesis of the derivatives of 1,2,4,5–tetrazine"; Acta Polonae Pharmaceutica; 50(2–3); 183–188; 1993 (abstract only).

\*1\* Schatz AR et al; "Cannabinoid receptors CB1 and CB2: a characterization of expression and adenylate cyclase modulation within the immune system"; Toxicol Appl Pharmacol. Feb. 1997; 142(2):278–87.

\*\*\* Schuel, H., Burkman, L.J., Picone, R.P., Bo, T., Makriyannis, A., *Cannabinoid receptors in human sperm. Mol. Biol. Cell.*, (1997) (8), 325a.

\*\*\* Serdarevich B., Caroll K.K., *"Synthesis and characterization of 1– and 2–monoglycerides of anteiso fatty acids"; J. Lipids Res.*; 7; 277–284; (1966).

Shawali, A.S., Albar, H.A.; "Kinetics and mechanism of dehydrochlorination of N–aryl–C–ethoxycarbonyl formohydrazidoyl chlorides"; Canadian Journal Of Chemistry; 64(5); 871–875; 1986 (abstract only).

\*\*\* Shen M. Thayer SA: *Cannabinoid receptor agonists protect cultured rat hippocampal neurons from excitotoxicity. Mol. Pharmacol (1996) 54*:459–462.

Shim et al; "Three–dimensional quantitative structure–activity relationship study of the cannabimimetic (aminoalkyl)indoles using comparative molecular field analysis"; J. Med. Chem.; 1998, 41(23); 4521–4532; XP–002212407.

Shim et al; "Unified pharmacophoric model for cannabinoids and aminoalkylindoles derived from molecular superimposition of CB1 cannabinoid receptor agonists CP55244 and WIN55212–2"; ACS Symposium series, 1999 719 (rational drug design), 165–184; XP–001095771.

Showalter et al; "Evaluation of binding in a transfected cell line expressing a peripheral cannabinoid receptor (CB2): identification of cannabinoid receptor subtype selective ligands"; J. Pharmacol. Exp. Ther., 1996 278(3) 989–999; XP–001097918.

\*\*\* Simiand J, Keane M, Keane PE, Soubrie P: *SR 141716, A CB1 cannabinoid receptor antagonist, selectively reduces sweet food intake in marmoset. Behav. Pharmacol (1998) 9*:179–181.

Smith P.B. et al; "The pharmacological activity of anandamide, a putative endogenous cannabinoid, in mice"; Journal of Pharmacology and Experimental Therapeutics; vol. 270(1):219–227; 1994.

Tetko, I. V. et al; "Volume Learning Algoritm Artificial Neural Networks For 3D QSAR Studies"; J. Med. Chem.; vol. 44, No. 15 (2001) pp. 2411–2420, 2413, 2414 Table 1.

\*\*\* Terranova J–P, Storme J–J Lafon N et al; *"Improvement of memory in rodents by the selective CB1 cannabinoid receptor antagonist, SR 141716"; Psycho–pharmacol (1996) 126*:165–172.

\*1\* Tius et al; "Conformationally restricted hybrids of CP–55,940 and HHC: Steroeselective synthesis and activity"; Tetrahedron; 50 (9); 2671–2680; (1994) (abstract only).

Twitchell, W. et al; "Cannabinoids inhibit N– and P/Q type calcium channels in cultured rat hippocampal neurons"; Journal of Neurophysiology; 78(1); 43–50; 1997 (abstract only).

\*1\* \*\*\* Ueda, N., *Endocannabinoid hydrolases. Prostaglandins & Other Lipid Mediators 2002*;68–69:521–534.

\*\*\* Vogel Z., Barg J., Levy R., Saya D., Heldman E., Mechoulam R.; *"Anandamide, a brain endogenous compound, interacts specifically with cannabinoid receptors and inhibits adenylate cyclase"; J. Neurochem.; 61(1) 352–355;* (1993).

\*\*\* Wagner JA, Varga K, Jarai Z, Kunos G; '*Mesenteric vasodialtion mediated by endothelia anandamide receptors'; Hypertension (1999) 33*:429–434.

\*1\* Watanabe, T.; Miyaura, N.; and Suzuki, A.; "Synthesis of Sterically Hindered Biaryls via the Palladium Catalyzed Cross–Coupling Reaction of Arylboronic Acids or their Esters with Haloarenes"; Synlett 1992; 207–210.

Wiley et al; "Structure activity relationships of indole and pyrrole derived cannabinoids"; J. Pharmacol. Exp. Ther. 1998, 285(3), 995–1004; XP–001097982.

*1* Wilson et al; "9–nor–delta8–tetrahydrocannabinol, a cannabinoid of metabolic intersts"; J. Med. Chem.; 17(4); 475–476; (1974).

*1* Wilson et al; "Analgesic properties of the tetrahydrocannabinols, their metabolites and analogs"; J. Med. Chem.; 18(7); 700–703; (1975).

*1* Wilson et al; "9–nor–9–hydrohexahydrocannabinols. Synthesis, some behavioral and analgesic properties, and comparison with the tetrahydrocannabinols"; J. Med. Chem.; 19(9); 1165–1167; (1976).

Yamada et al; "(Aminoalkyl)indole isothiocyanates as potentiual electrophilic affinity ligands for the brain cannabinoid receptor"; J. Med. Chem. 1996, vol. 39(10), 1967–1974.

*1* Yan, Guo et al; "Synthesis and pharmacological properties of 11–hydroxy–3–(1'–1'–dimethylheptyl)hexahydrocannabinol: a high affinity cannabinoid agonist"; J. Med. Chem.; vol. 37(16); 2619–2622; (1994).

*1* Yan Guo et al; "(−)–11–hydroxy–7'–isothiocyanato–1'–1'dimethylheptyl–delta8–THC: a novel probe for the cannabinoid receptor in the brain"; J. Med. Chem.; 37(23); 3867–3870; (1994).

BICYCLIC AND TRICYCLIC CANNABINOIDS

This application is the U.S. National Stage of International Application No. PCT/US02/21961, filed Jul. 11, 2002, which claims the benefit of U.S. Provisional Application No. 60/305,228, filed Jul. 13, 2001, the contents of each of which are incorporated herein by reference in their entirety.

FIELD OF THE INVENTION

The present invention relates generally to cannabinoid analogs. The invention is more particularly concerned with new and improved bicyclic and tricyclic cannabinoids exhibiting high binding affinities for cannabinoid receptors, pharmaceutical preparations employing these analogs and methods of administering therapeutically effective amounts of the analogs to provide a physiological effect.

BACKGROUND OF THE INVENTION

The classical cannabinoid $\Delta^9$-Tetrahydrocannabinol ($\Delta^9$-THC) is the major active constituent extracted from *Cannabis sativa*. The effects of cannabinoids are due to an interaction with specific high-affinity receptors. Presently, two cannabinoid receptors have been characterized: CB1, a central receptor found in the mammalian brain and a number of other sites in the peripheral tissues and CB2, a peripheral receptor found principally in cells related to the immune system. The CB1 receptor is believed to mediate the psychoactive properties, associated with classical cannabinoids. Characterization of these receptors has been made possible by the development of specific synthetic ligands such as the agonists WIN 55212-2 and CP 55,940.

In addition to acting at the cannabinoid receptors, cannabinoids such as $\Delta^9$-THC also affect cellular membranes, thereby producing undesirable side effects such as drowsiness, impairment of monoamine oxidase function and impairment of non-receptor mediated brain function. The addictive and psychotropic properties of some cannabinoids also limit their therapeutic value.

The pharmacological effects of cannabinoids pertain to a variety of areas such as the central nervous system, the cardiovascular system, the immune system and/or endocrine system. More particularly, compounds possessing an affinity for either the CB1 or the CB2 cannabinoid receptors are useful as agents: acting on the central nervous system and immunomodulators; in thymic disorders; vomiting; myorelaxation; various types of neuropathy; memory disorders; dyskinesia; migraine; multiple sclerosis; asthma; epilepsy; glaucoma; in anticancer chemotherapy; in ischemia and angor; in orthostatic hypotension; and in cardiac insufficiency.

Currently known bicyclic-cannabinoids and hexahydrocannabinol analogs contain a linear alkyl side chain at the C-3 position. This linear alkyl side chain at the C-3 position is a key pharmacophore in classical cannabinoids and considered essential for cannabinoid receptor activity. Structure Activity Relationship (SAR) studies suggest that in known cannabinoids, a 1,1-dimethylheptyl or a 1,2-dimethylheptyl side chain is optimal for cannabinoid activity. Additionally, known hexahydrocannabinol derivatives usually possess a carbonyl group in the C-9 position or a hydroxy group in the C-9 or C-11 positions. This "northern" functionality plays an important role on the cannabinoid structure, associated with cannabimimetic activity. The presence of a C-9 carbonyl group or a C-9 or C-11 hydroxy group is also known to significantly enhance the potency of cannabinoids.

SUMMARY OF THE INVENTION

Briefly stated, one aspect of the present invention comprises novel bicyclic-cannabinoids and hexahydrocannabinol analogs, and their physiologically acceptable salts. In some variations the inventive hexahydrocannabinol analogs include hitherto unknown side chain moieties at the C-3 position. In some variations the inventive hybrid type bicyclic-cannabinoids have terpene functionality combined with novel resorcinol moieties. The invention includes both the (−) and (+) enantiomers and all isomers. Some embodiments of this aspect are represented by the following compound formulas I, II, III, IV, V, VI.

Compound Formula I

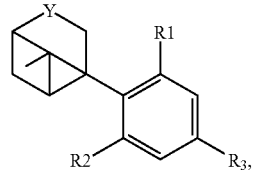

I wherein Y comprises >C=O, >CH—(CH$_2$)$_f$—Y$_1$—(CH$_2$)$_g$—Y$_2$, >C=N—Y$_3$, >CH—NY$_4$Y$_5$, >CH—(CH$_2$)$_h$—Y$_6$, —C(O)N(Y$_7$)—, —N(Y$_7$)C(O)—, >NY$_{11}$, >N—(CH$_2$)$_f$—Y$_1$—(CH$_2$)$_g$—Y$_2$, a spirocycle, or CY$_9$Y$_{10}$, including all isomers.

Y$_1$ independently comprises O, CO, C(O)O, OCO or CH$_2$.

Y$_2$ independently comprises H, halogen, CN, CF$_3$, N$_3$, OH, COOH, alkoxy, acyloxy, NCS, NCO or NY$_7$Y$_8$.

Y$_3$ independently comprises —OH, —NH$_2$, alkoxy, alkyl, —(CH$_2$)$_n$—NR$_{10}$R$_{11}$, —(CH$_2$)$_n$—CO$_2$R where R comprises H or alkyl, —O—(CH$_2$)$_n$—NR$_{10}$R$_{11}$, —O—(CH$_2$)$_n$—CO$_2$R or —O—(CH$_2$)$_n$—CONR$_{10}$R$_{11}$.

Y$_4$ independently comprises H, OH, alkoxy or alkyl.

Y$_5$ independently comprises H, OH, alkoxy or alkyl, wherein Y$_4$ and Y$_5$ cannot both be OH and wherein Y$_4$ and Y$_5$ cannot both be alkoxy.

Y$_6$ independently comprises H, halogen, CN, COOH, COalkyl, CF$_3$, SO$_2$alkyl, COfluoroalkyl, N$_3$, OH, alkoxy, acyloxy, NCS, NCO or NY$_7$Y$_8$.

Y$_7$ independently comprises H, alkyl, hydroxyalkyl, an aromatic ring, an aromatic ring substituted by at least one member selected from alkyl, alkoxy, halogen and CF$_3$, a heterocyclic ring or a heteroaromatic ring.

Y$_8$ independently comprises H, alkyl, hydroxyalkyl, an aromatic ring, an aromatic ring substituted by at least one member selected from alkyl, alkoxy, halogen and CF$_3$, a heterocyclic ring or a heteroaromatic ring. Alternatively, Y$_7$ and Y$_8$ taken together comprise part of a 3 to 7 membered saturated heterocyclic ring containing up to one additional heteroatom selected from N, O and S.

Y$_9$ independently comprises H, alkyl or alkoxycarbonylmethyl.

Y$_{10}$ independently comprises H, alkyl or alkoxycarbonylmethyl.

Y$_{11}$ independently comprises H, alkyl, CO, CN, CO-alkyl, SO$_2$-alkyl or CF$_3$. f comprises an integer from 0 to about 5.

g comprises an integer from 0 to about 5.

h comprises an integer from 0 to about 5.

n comprises an integer from 0 to about 4.

R$_1$ and R$_2$ each independently comprise H, OH, halogen, alkyl, —O-alkyl, NH$_2$, NO$_2$, CN, acyl, aroyl, benzoyl, substituted benzoyl, arylalkyl, substituted arylalkyl, phenacyl, substituted phenacyl, —O-alkyl-$NR_{10}R_{11}$, —O-alkyl-COOR where R comprises H or alkyl, —O-alkyl-$CONR_{10}R_{11}$, $OCOCH_3$, —N(alkyl)$_2$, —CO(alkyl)X or —OCO(alkyl)X where X comprises H, dialkylamino, a cyclic amine, a carbocyclic ring, a heterocyclic ring, an aromatic ring or a heteroaromatic.

$R_{10}$ and $R_{11}$ each independently comprise H, alkyl, hydroxyalkyl or $R_{10}$ and $R_{11}$ together comprise part of a 3 to 7 membered saturated heterocyclic ring containing up to one additional heteroatom selected from N, O and S.

$R_3$ comprises

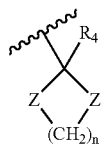

wherein each Z independently comprises $CR_{12}R_{13}$ where $R_{12}$ and $R_{13}$ each independently comprise H, alkyl, S, O, NH, N(CH$_3$), SO or SO$_2$.

$R_4$ comprises —(CH$_2$)$_j$—$R_5$, —(CH$_2$)$_j$-A-(CH$_2$)$_k$—$R_5$ or —(CH$_2$)$_j$-A-(CH$_2$)$_k$-B-$R_5$.

A and B each independently comprise —CH$_2$—CH$_2$—, —CH=CH—, —C≡C—, O, S, SO, SO$_2$ or NH.

$R_5$ comprises H, halogen, CN, CF$_3$, N$_3$, COOH, NH$_2$, N(CH$_3$)$_2$, ⊕N(CH$_3$)$_3$, Sn(alkyl)$_3$, phenyl, COOR where R comprises H or alkyl, a carbocylic ring, a heterocyclic ring, an aromatic ring, a heteroaromatic ring, a polycarbocyclic ring structure having 2 to about 5 rings, a polyheterocyclic ring structure having 2 to about 5 rings or $CONR_{10}R_{11}$ where $R_{10}$ and $R_{11}$ each independently comprise H, alkyl, hydroxyalkyl or $R_{10}$ and $R_{11}$ together comprise part of a 5 or 6 membered saturated heterocyclic ring containing up to one additional heteroatom selected from N, O and S.

n comprises an integer from 0 to about 4.
j comprises an integer from 0 to about 7.
k comprises an integer from 0 to about 7.

In one variation of the invention $R_3$ comprises

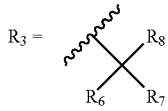

wherein $R_6$ and $R_7$ each independently comprise H or alkyl.

$R_8$ comprises —(CH$_2$)$_j$—C≡C—(CH$_2$)$_k$—$R_9$.

$R_9$ comprises H, halogen, CN, CF$_3$, N$_3$, COOH, NH$_2$, N(CH$_3$)$_2$, ⊕N(CH$_3$)$_3$, Sn(alkyl)$_3$, phenyl, COOR where R comprises H or alkyl, a carbocylic ring, a heterocyclic ring, an aromatic ring, a heteroaromatic ring, a polycarbocyclic ring structure having 2 to about 5 rings, a polyheterocyclic ring structure having 2 to about 5 rings or $CONR_{10}R_{11}$ where $R_{10}$ and $R_{11}$ each independently comprise H, alkyl, hydroxyalkyl or $R_{10}$ and $R_{11}$ together comprise part of a 5 or 6 membered saturated heterocyclic ring containing up to one additional heteroatom selected from N, O and S. j comprises an integer from 0 to about 7. k comprises an integer from 0 to about 7.

In another variation of the invention (compound formula II) $R_1$ and $R_2$ each independently comprise H, OH, alkyl or alkoxy and $R_3$ comprises:

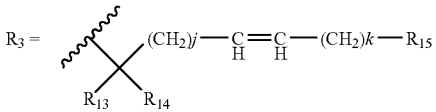

wherein $R_{13}$ and $R_{14}$ each independently comprise H or alkyl.

$R_{15}$ comprises H, halogen, CN, CF$_3$, N$_3$, COOH, NH$_2$, N(CH$_3$)$_2$, ⊕N(CH$_3$)$_3$, Sn(alkyl)$_3$, phenyl, COOR where R comprises H or alkyl, a carbocylic ring, a heterocyclic ring, an aromatic ring, a heteroaromatic ring, a polycarbocyclic ring structure having 2 to about 5 rings, a polyheterocyclic ring structure having 2 to about 5 rings or $CONR_{10}R_{11}$ where $R_{10}$ and $R_{11}$ each independently comprise H, alkyl, hydroxyalkyl or $R_{10}$ and $R_{11}$ together comprise part of a 5 or 6 membered saturated heterocyclic ring containing up to one additional heteroatom selected from N, O and S.

j comprises an integer from 0 to about 7.
k comprises an integer from 0 to about 7.

In another variation of the invention (compound formula III) Y comprises >CH—(CH$_2$)$_h$—Y$_6$.

Y$_6$ comprises I, CN or N$_3$ and h comprises an integer from about 1 to about 3, or Y$_6$ comprises I or N$_3$ and h comprises an integer from 0 to about 3.

$R_1$ and $R_2$ each independently comprise H, OH, alkyl or alkoxy.

$R_3$ comprises:

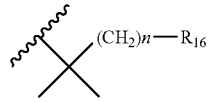

wherein $R_{16}$ comprises H, halogen, CN, CF$_3$, N$_3$, COOH, NH$_2$, N(CH$_3$)$_2$, ⊕N(CH$_3$)$_3$, Sn(alkyl)$_3$, phenyl, COOR where R comprises H or alkyl, a carbocyclic ring, a heterocyclic ring, an aromatic ring, a heteroaromatic ring, a polycarbocyclic ring structure having 2 to about 5 rings, a polyheterocyclic ring structure having 2 to about 5 rings or $CONR_{10}R_{11}$ where $R_{10}$ and $R_{11}$ each independently comprise H, alkyl, hydroxyalkyl or $R_{10}$ and $R_{11}$ together comprise part of a 5 or 6 membered saturated heterocyclic ring containing up to one additional heteroatom selected from N, O and S.

n comprises an integer from 0 to about 7.

Another variation of the invention (compound formula IV) has the following structure:

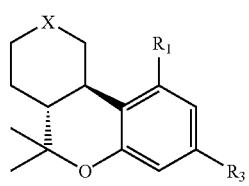

wherein X comprises >C=O, >CH——(CH$_2$)$_f$—X$_1$—(CH$_2$)$_g$—X$_2$, >C=N—X$_3$, >CH—NX$_4$X$_5$, >CH—(CH$_2$)$_h$—X$_6$, —C(O)N(X$_7$)—, —N(X$_7$)C(O)—, >NX$_{11}$, >N—(CH$_2$)$_f$—X$_1$—(CH$_2$)$_g$—X$_2$, a spirocycle, or CX$_9$X$_{10}$, including all isomers.

$X_1$ independently comprises O, CO, C(O)O, OCO or $CH_2$.

$X_2$ independently comprises H, halogen, CN, $CF_3$, $N_3$, OH, COOH, alkoxy, acyloxy, NCS, NCO or $NX_7X_8$.

$X_3$ independently comprises —OH, —$NH_2$, alkoxy, alkyl, —$(CH_2)_n$—$NR_{10}R_{11}$, —$(CH_2)_n$—$CO_2R$ where R comprises H or alkyl, —O—$(CH_2)_n$—$NR_{10}R_{11}$, —O—$(CH_2)_n$—$CO_2R$ or —O—$(CH_2)_n$—$CONR_{10}R_{11}$.

$X_4$ independently comprises H, OH, alkoxy or alkyl.

$X_5$ independently comprises H, OH, alkoxy or alkyl, wherein $X_4$ and $X_5$ cannot both be OH and wherein $X_4$ and $X_5$ cannot both be alkoxy.

$X_6$ independently comprises H, halogen, CN, COOH, COalkyl, $CF_3$, $SO_2$alkyl, COfluoroalkyl, $N_3$, OH, alkoxy, acyloxy, NCS, NCO or $NX_7X_8$.

$X_7$ independently comprises H, alkyl, hydroxyalkyl, an aromatic ring, ar aromatic ring substituted by at least one member selected from alkyl, alkoxy, halogen and $CF_3$, a heterocyclic ring or a heteroaromatic ring.

$X_8$ independently comprises H, alkyl, hydroxyalkyl, an aromatic ring, an aromatic ring substituted by at least one member selected from alkyl, alkoxy, halogen and $CF_3$, a heterocyclic ring or a heteroaromatic ring. Alternatively, $X_7$ and $X_8$ taken together comprise part of a 3 to 7 membered saturated heterocyclic ring containing up to one additional heteroatom selected from N, O and S.

$X_9$ independently comprises H, alkyl or alkoxycarbonylmethyl.

$X_{10}$ independently comprises H, alkyl or alkoxycarbonylmethyl.

$X_{11}$ independently comprises H, alkyl, CO, CN, COalkyl, $SO_2$alkyl or $CF_3$.

f comprises an integer from 0 to about 3.

g comprises an integer from 0 to about 3.

h comprises an integer from 0 to about 3.

n comprises an integer from 0 to about 4.

$R_1$ independently comprises H, OH, halogen, alkyl, —O-alkyl, $NH_2$, $NO_2$, CN, acyl, aroyl, benzoyl, substituted benzoyl, arylalkyl, substituted arylalkyl, phenacyl, substituted phenacyl, —O-alkyl-$NR_{10}R_{11}$, —O-alkyl-COOR where R comprises H or alkyl, —O-alkyl-$CONR_{10}R_{11}$, $OCOCH_3$, —N(alkyl)$_2$, —CO(alkyl)X or —OCO(alkyl)X where X comprises H, dialkylamino, a cyclic amine, a carbocyclic ring, a heterocyclic ring, an aromatic ring or a heteroaromatic.

$R_{10}$ and $R_{11}$ each independently comprise H, alkyl, hydroxyalkyl or $R_{10}$ and $R_{11}$ together comprise part of a 3 to 7 membered saturated heterocyclic ring containing up to one additional heteroatom selected from N, O and S.

$R_3$ comprises

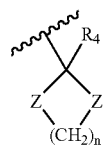

wherein each Z independently comprises $CR_{12}R_{13}$ where $R_{12}$ and $R_{13}$ each independently comprise H, alkyl, S, O, NH, N(CH$_3$), SO or SO$_2$.

$R_4$ comprises —$(CH_2)_j$—$R_5$, —$(CH_2)_j$-A-$(CH_2)_k$—$R_5$ or —$(CH_2)_j$-A-$(CH_2)_k$-B-$R_5$.

A and B each independently comprise —$CH_2$—$CH_2$—, —CH=CH—, —C≡C—, O, S, SO, SO$_2$ or NH.

$R_5$ comprises H, halogen, CN, $CF_3$, $N_3$, COOH, $NH_2$, N(CH$_3$)$_2$, ⊕N(CH$_3$)$_3$, Sn(alkyl)$_3$, phenyl, COOR where R comprises H or alkyl, a carbocylic ring, a heterocyclic ring, an aromatic ring, a heteroaromatic ring, a polycarbocyclic ring structure having 2 to about 5 rings, a polyheterocyclic ring structure having 2 to about 5 rings or $CONR_{10}R_{11}$ where $R_{10}$ and $R_{11}$ each independently comprise H, alkyl, hydroxyalkyl or $R_{10}$ and $R_{11}$ together comprise part of a 5 or 6 membered saturated heterocyclic ring containing up to one additional heteroatom selected from N, O and S.

n comprises an integer from 0 to about 4.

j comprises an integer from 0 to about 7.

k comprises an integer from 0 to about 7.

In one variation of the invention, $R_3$ comprises:

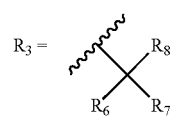

wherein $R_6$ and $R_7$ each independently comprise H or alkyl.

$R_8$ comprises —$(CH_2)_j$—C≡C—$(CH_2)_k$—$R_9$.

$R_9$ comprises H, halogen, CN, $CF_3$, $N_3$, COOH, $NH_2$, N(CH$_3$)$_2$, ⊕N(CH$_3$)$_3$, Sn(alkyl)$_3$, phenyl, COOR where R comprises H or alkyl, a carbocylic ring, a heterocyclic ring, an aromatic ring, a heteroaromatic ring, a polycarbocyclic ring structure having 2 to about 5 rings, a polyheterocyclic ring structure having 2 to about 5 rings or $CONR_{10}R_{11}$ where $R_{10}$ and $R_{11}$ each independently comprise H, alkyl, hydroxyalkyl or $R_{10}$ and $R_{11}$ together comprise part of a 5 or 6 membered saturated heterocyclic ring containing up to one additional heteroatom selected from N, O and S.

j comprises an integer from 0 to about 7.

k comprises an integer from 0 to about 7.

In another variation of the invention (compound formula V) $R_1$ comprises H, OH, alkyl or alkoxy and $R_3$ comprises:

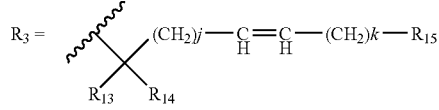

wherein $R_{13}$ and $R_{14}$ each independently comprise H or alkyl.

$R_{15}$ comprises halogen, CN, $CF_3$, $N_3$, COOH, $NH_2$, N(CH$_3$)$_2$, ⊕N(CH$_3$)$_3$, Sn(alkyl)$_3$, phenyl, COOR where R comprises H or alkyl, a carbocylic ring, a heterocyclic ring, an aromatic ring, a heteroaromatic ring, a polycarbocyclic ring structure having 2 to about 5 rings, a polyheterocyclic ring structure having 2 to about 5 rings or $CONR_{10}R_{11}$ where $R_{10}$ and $R_{11}$ each independently comprise H, alkyl, hydroxyalkyl or $R_{10}$ and $R_{11}$ together comprise part of a 5 or 6 membered saturated heterocyclic ring containing up to one additional heteroatom selected from N, O and S.

j comprises an integer from 0 to about 7.

k comprises an integer from 0 to about 7.

In another variation of the invention (compound formula VI) X comprises >CH—$(CH_2)_h$—$X_6$.

$X_6$ independently comprises I, CN, $N_3$ or COOH and h comprises an integer from about 1 to about 3, or $X_6$ comprises I, $N_3$ or COOH and h comprises an integer from 0 to about 3, including all isomers.

$R_1$ independently comprises H, OH, alkyl or alkoxy.

$R_3$ comprises:

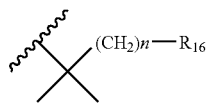

$R_{16}$ comprises H, halogen, CN, $CF_3$, $N_3$, COOH, $NH_2$, $N(CH_3)_2$, $\oplus N(CH_3)_3$, $Sn(alkyl)_3$, phenyl, COOR where R comprises H or alkyl, a carbocylic ring, a heterocyclic ring, an aromatic ring, a heteroaromatic ring, a polycarbocyclic ring structure having 2 to about 5 rings, a polyheterocyclic ring structure having 2 to about 5 rings or $CONR_{10}R_{11}$ where $R_{10}$ and $R_{11}$ each independently comprise H, alkyl, hydroxyalkyl or $R_{10}$ and $R_{11}$ together comprise part of a 5 or 6 membered saturated heterocyclic ring containing up to one additional heteroatom selected from N, O and S.

n comprises an integer from 0 to about 7.

Unless otherwise specifically defined, "acyl" refers to the general formula —C(O)alkyl.

Unless otherwise specifically defined, "acyloxy" refers to the general formula —O-acyl.

Unless otherwise specifically defined, "alcohol" refers to the general formula alkyl-OH.

Unless otherwise specifically defined, "alkyl" refers to a linear, branched or cyclic alkyl group having from 1 to about 9 carbon atoms including, for example, methyl, ethyl, propyl, butyl, hexyl, octyl, isopropyl, isobutyl, tert-butyl, cyclopropyl, cyclohexyl, cyclooctyl, vinyl and allyl. Unless otherwise specifically defined, an alkyl group can be saturated or unsaturated and substituted or unsubstituted. Unless otherwise specifically limited, a cyclic alkyl group includes monocyclic, bicyclic and polycyclic rings, for example norbornyl, adamantyl and related terpenes.

Unless otherwise specifically defined, "alkoxy" refers to the general formula —O-alkyl.

Unless otherwise specifically defined, "alkylmercapto" refers to the general formula —S-alkyl.

Unless otherwise specifically defined, "alkylamino" refers to the general formula —(NH)-alkyl.

Unless otherwise specifically defined, "di-alkylamino" refers to the general formula $—N-(alkyl)_2$. Unless otherwise specifically limited di-alkylamino includes cyclic amine compounds such as piperidine and morpholine.

Unless otherwise specifically defined, an aromatic ring is an unsaturated ring structure having about 5 to about 6 ring members and including only carbon as ring atoms. Unless otherwise specifically defined, an aromatic ring can be substituted or unsubstituted.

Unless otherwise specifically defined, "aryl" refers to an aromatic ring system substituted or unsubstituted, that includes only carbon as ring atoms, for example phenyl, biphenyl or napthyl.

Unless otherwise specifically defined, "aroyl" refers to the general formula —C(=O)-aryl.

Unless otherwise specifically defined, a carbocyclic ring is a ring structure having about 3 to about 8 ring members, substituted or unsubstituted, that includes only carbon as ring atoms, for example, benzene or cyclohexane.

Unless otherwise specifically defined, "halogen" refers to an atom selected from fluorine, chlorine, bromine and iodine.

Unless otherwise specifically defined, a heteroaromatic ring is an unsaturated ring structure having about 5 to about 8 ring members, substituted or unsubstituted, that has carbon atoms and one or more heteroatoms, including oxygen, nitrogen and/or sulfur, as ring atoms, for example, pyridine, furan, quinoline, and their derivatives.

Unless otherwise specifically defined, a heterocyclic ring is a saturated ring structure having about 3 to about 8 ring members, substituted or unsubstituted, that has carbon atoms and one or more heteroatoms, including oxygen, nitrogen and/or sulfur, as ring atoms, for example, piperidine, morpholine, piperazine, and their derivatives. Unless otherwise specifically limited a heterocyclic ring includes monocyclic, bicyclic and polycyclic rings, for example azaadamantyl and tropanyl.

Unless otherwise specifically defined, the term "phenacyl" refers to the general formula -phenyl-acyl.

Unless otherwise specifically defined, a spirocycle refers to a ring system wherein a single atom is the only common member of two rings. A spirocycle can comprise a saturated carbocyclic ring comprising about 3 to about 8 ring members, a heterocyclic ring comprising about 3 to about 8 ring atoms wherein up to about 3 ring atoms may be N, S, or O or a combination thereof.

Substituent groups for the above moieties-useful in the invention are those groups that do not significantly diminish the biological activity of the inventive compound. Substituent groups that do not significantly diminish the biological activity of the inventive compound include, for example, —OH, —$NH_2$, halogen, —CN, —$NO_2$, —NHalkyl, —$N(alkyl)_2$, —$CF_3$, —NCS, azido, —CONHalkyl, —NHCOalkyl, sulfonamide, alkyl, alkoxy, thioalkoxy and alcohol.

Testing of the inventive compounds for their affinities for the central (CB1) and peripheral (CB2) cannabinoid receptors, showed a high affinity for the two cannabinoid receptors. Thus, another aspect of the invention is use of at least one of the inventive compounds, and physiologically acceptable salts thereof, to stimulate cannabinoid receptors.

Some of the inventive analogs showed high selectivity for the CB2 receptor. These inventive CB2 selective analogs are able to stimulate the CB2 receptor without affecting the central (CB1) receptor to the same degree. Therefore, another aspect of the invention is use of at least one of the inventive compounds, and physiologically acceptable salts thereof, to preferentially stimulate the CB2 receptor.

The inventive bicyclic-cannabinoids and hexahydrocannabinol analogs described herein, and physiologically acceptable salts thereof, have pharmacological properties when administered in therapeutically effective amounts for providing a physiological effect useful to treat central and peripheral pain, neuropathy, neurodegenerative diseases including multiple sclerosis, Parkinson's disease, Huntington's chorea, Alzheimer's disease; mental disorders such as schizophrenia and depression; to prevent or reduce endotoxic shock and hypotensive shock; to modulate appetite; to modulate the immune system; to reduce fertility; to prevent or reduce diseases associated with motor function such as Tourette's syndrome; to prevent or reduce inflammation; to provide neuroprotection and to suppress memory and produce peripheral vasodilation; to treat epilepsy, glaucoma, nausea associated with cancer chemotherapy and AIDS wasting syndrome as well as other ailments in which cannabinoid system is implicated. Thus, another aspect of the invention is the administration of a therapeutically effective amount of an inventive compound, or a physiologically acceptable salt thereof, to an individual or animal to provide a physiological effect.

DESCRIPTION OF SOME PREFERRED EMBODIMENTS

As used herein a "therapeutically effective amount" of a compound, is the quantity of a compound which, when administered to an individual or animal, results in a discernible physiological effect in the individual or animal. The inventive compounds described herein, and physiologically acceptable salts thereof, have pharmacological properties when administered in therapeutically effective amounts for providing a physiological effect useful to treat a number of physiological conditions.

Typically, a "therapeutically effective amount" of an inventive compound is believed to range from about 5 mg/day to about 1,000 mg/day.

As used herein, an "individual" refers to a human. An "animal" refers to, for example, veterinary animals, such as dogs, cats, horses and the like, and farm animals, such as cows, pigs and the like.

The compound of the present invention can be administered by a variety of known methods, including, for example, orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular, subcutaneous, ocular, intranasal, inhalation-based and transdermal administration) and slow releasing microcarriers (for rectal, intramuscular or intravenous administration). The formulations can also contain a physiologically acceptable vehicle and optional adjuvants, flavorings, colorants and preservatives. Suitable physiologically acceptable vehicles include, for example, saline, sterile water, Ringer's solution and isotonic sodium chloride solutions. The specific dosage level of active ingredient will depend upon a number of factors, including, for example, biological activity of the particular preparation, age, body weight, sex and general health of the individual being treated.

In one aspect of the invention the inventive compounds are generally represented by compound formulas I, II, III, IV, V, VI and include physiologically acceptable salts thereof.

Compound Formulas I–VI

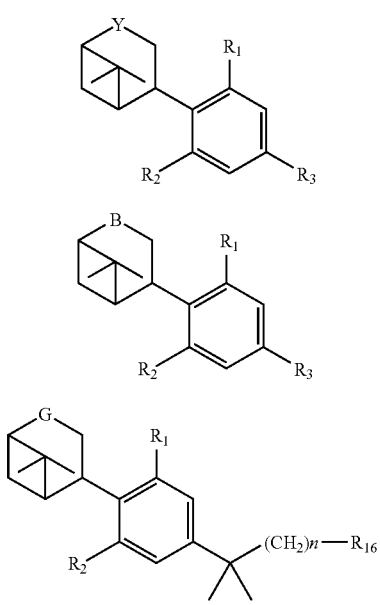

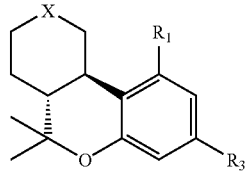

IV

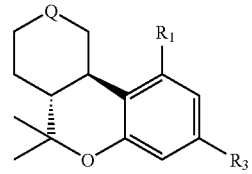

V

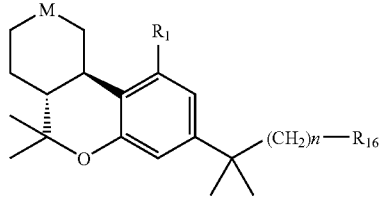

VI

Some inventive analogs were tested for CB2 receptor binding affinity and for CB1 receptor affinity (to determine selectivity). As used herein, "binding affinity" is represented by the $IC_{50}$ value which is the concentration of an analog required to occupy the 50% of the total number (Bmax) of the receptors. The lower the $IC_{50}$ value the higher the binding affinity. As used herein an analog is said to have "binding selectivity" if it has higher binding affinity for one receptor compared to the other receptor; e.g. a cannabinoid analog which has an $IC_{50}$ of 0.1 nM for CB1 and 10 nM for CB2, is 100 times more selective for the CB1 receptor. For the CB1 receptor binding studies, membranes were prepared from rat forebrain membranes according to the procedure of P. R. Dodd et al, *A Rapid Method for Preparing Synaptosomes: Comparison with Alternative Procedures*, Brain Res., 107–118 (1981). The binding of the novel analogues to the CB1 cannabinoid receptor was assessed as described in W. A. Devane et al, *Determination and Characterization of a Cannabinoid Receptor in a Rat Brain*, Mol. Pharmacol., 34, 605–613 (1988) and A. Charalambous et al, *5′-azido $\Delta^8$-THC: A Novel Photoaffinity Label for the Cannabinoid Receptor*, J. Med. Chem., 35, 3076–3079 (1992) with the following changes. The above articles are incorporated by reference herein.

Membranes, previously frozen at −80° C., were thawed on ice. To the stirred suspension was added three volumes of TME (25 mM Tris-HCl buffer, 5 mM $MgCl_2$ and 1 mM EDTA) at a pH 7.4. The suspension was incubated at 4° C. for 30 min. At the end of the incubation, the membranes were pelleted and washed three times with TME.

The treated membranes were subsequently used in the binding assay described below. Approximately 30 μg of membranes were incubated in silanized 96-well microtiter plate with TME containing 0.1% essentially fatty acid-free bovine serum albumin (BSA), 0.8 nM [$^3$H] CP-55,940, and various concentrations of test materials in a final volume of 200 μL. The assays were incubated for 1 hour at 30° C. and then immediately filtered using Packard Filtermate 196 harvester and Whatman GF/C filterplates and washed with wash buffer (TME) containing 0.5% BSA. Radioactivity was detected using MicroScint 20 scintillation cocktail added directly to the dried filterplates, and the filterplates were counted using a Packard Instruments Top-Count. Non-specific binding was assessed using 100 nM CP-55,940. Data collected from three independent experiments performed with duplicate determinations was normalized between 100% and 0% specific binding for [$^3$H] CP-55,940, determined using buffer and 100 nM CP-55,940. The normalized data was analyzed using a 4-parameter nonlinear logistic equation to yield IC$_{50}$ values. Data from at least two independent experiments performed in duplicate was used to calculate IC$_{50}$ values which were converted to K$_I$ values using the assumptions of Cheng et al, *Relationship Between the Inhibition Constant (K$_I$) and the concentration of Inhibitor which causes 50% Inhibition (IC$_{50}$) of an Enzymatic Reaction*, Biochem. Pharmacol., 22, 3099–3102, (1973), which is incorporated by reference herein.

For the CB2 receptor binding studies, membranes were prepared from frozen mouse spleen essentially according to the procedure of P. R. Dodd et al, *A Rapid Method for Preparing Synaptosomes: Comparison with Alternative Procedures*, Brain Res., 226, 107–118 (1981) which is incorporated by reference herein. Silanized centrifuge tubes were used throughout to minimize receptor loss due to adsorption. The CB2 binding assay was conducted in the same manner as for the CB1 binding assay. The binding affinities (K$_I$) were also expressed in nanomoles (nM). Some of the synthesized analogs disclosed below exhibited a selectivity for the CB2 receptor of from less than 10 fold to about 500 fold. Some of the synthesized analogs disclosed below exhibited a lesser selectivity for the CB1 receptor.

The following examples are given for purposes of illustration only in order that the present invention may be more fully understood. These examples are not intended to limit in any way the scope of the invention unless otherwise specifically indicated.

EXAMPLES

Bicyclic-cannabinoid hybrids of compound formula I, II and III were synthesized with different R groups and different Y, B, G functionalities are depicted in Table 1. The CB1 and CB2 binding affinity value (Ki) for the synthesized analogs range between 31–224 nM and 0.2–77 nM respectively.

TABLE 1

Novel Bicyclic-cannabinoid analogs of compound formula I, II and III.

| Compound number | Y Functionality | R$_1$ | R$_2$ | R$_3$ | CB1 Receptor Ki (nM) | CB2 Receptor Ki (nM) |
|---|---|---|---|---|---|---|
| 2a | C=O (dimethyl) | OH | OH | 1,1-cyclopentyl with n-pentyl chain | 50.6 | 0.4 |
| 2b | C=O (dimethyl) | OH | OH | 1,1-cyclopentyl with pentenyl chain | 74.5 | 0.4 |
| 2c | C=O (dimethyl) | OH | OH | 1,3-dithiolane with n-pentyl chain | 223.5 | 10.9 |
| 2d | C=O (dimethyl) | OH | OH | dimethyl with bromoalkyl chain (Br terminus) | 10.6 | 9.3 |
| 2e | C=O (dimethyl) | OH | OH | dimethyl with terminal alkyne chain | 30.8 | 0.2 |
| 3 | CH(H)—OH | OH | OH | 1,3-dithiolane with n-pentyl chain | 133.2 | 76.8 |

Hexahydrocannabinol derivatives of compound formula IV, V and VI were synthesized with different R groups and different X, Q, M functionalities are depicted in Table 2. The CB1 and CB2 binding affinity value (Ki) for the synthesized analogs range between 0.1–12 nM and 0.2–14 nM respectively.

TABLE 2
Novel Hexahydrocannabinol analogs of compound formula IV, V and VI.
| Compound number | X Functionality | R₁ | R₃ | CB1 Receptor Ki (nM) | CB,2 Receptor Ki (nM) |
|---|---|---|---|---|---|
| 4a |  | OH | 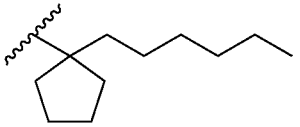 | 0.1 | 2.6 |
| 4b |  | OH |  | 0.2 | 0.2 |
| 4c | 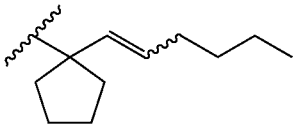 | OH |  | 11.7 | 2.3 |
| 4d |  | OH | 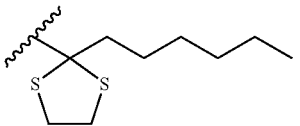 | 1.0 | 11.8 |
| 4e |  | OH |  | 10.7 | 4.1 |
| 5 | 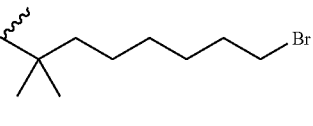 | OH |  | 4.5 | 13.9 |
| 6d |  | OH | 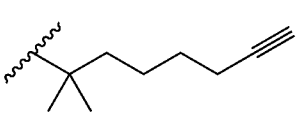 | — | — |
| 6e |  | OH |  | 11.3 | 12 |
| 6f | 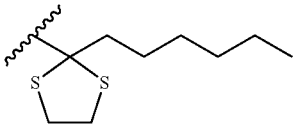 | OH |  | — | — |
| 7d |  | OH | 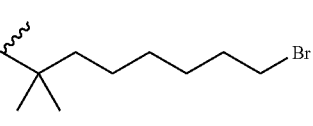 | 1.6 | 13.7 |
| 7f |  | OH |  | — | — |
| 7g | 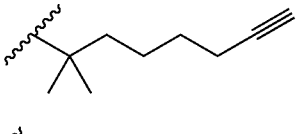 | OH |  | 5.0 | 10.2 |

TABLE 2-continued

Novel Hexahydrocannabinol analogs of compound formula IV, V and VI.

| Compound number | X Functionality | $R_1$ | $R_3$ | CB1 Receptor Ki (nM) | CB,2 Receptor Ki (nM) |
|---|---|---|---|---|---|
| 8 | ⟩C(H)—N₃ | OH | (gem-dimethyl)—(CH₂)₅—I | 0.8 | 0.9 |
| 9 | ⟩C(H)—N₃ | OH | (gem-dimethyl)—(CH₂)₂—CH=CH—CH₂I | 0.7 | 0.7 |

Preparation of Compounds of Compound Formula I, II, III

1. Resorcinol Synthesis

Resorcinol compounds 1a and 1b (shown in Scheme 1) were synthesized by a method depicted in Scheme 1, starting from (3,5-dimethoxyphenyl)cyclopentane carboxaldehyde, which was prepared by the method disclosed in Papahatjis et al. *Chemistry Letters*, 192 (2001), the content of which is hereby incorporated by reference.

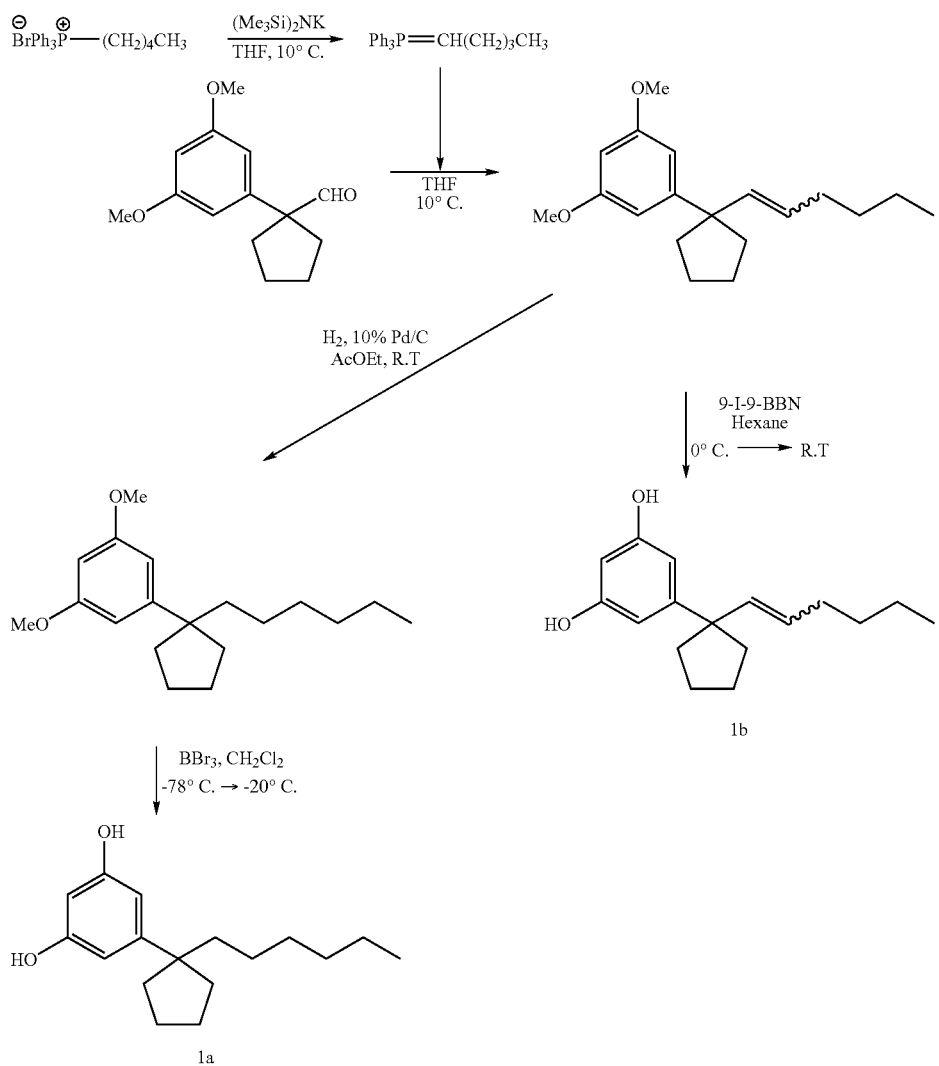

Scheme 1

General Procedure:
(Butylmethylene) triphenylphosphorane.

To a suspension of pentyltriphenylphosphonium bromide (5 equiv.) in dry THF (0.18M) at 0° C., under an argon atmosphere was added potassium bis(trimethylsilyl) amide (4.9 equiv.). The mixture was warmed to 10° C. and stirred for an additional 30 min to ensure complete formation of the orange ylide. The resulting slurry was used in the preparation of 1-(3,5-dimethoxyphenyl)-1-(hex-1-enyl)-cyclopentane.

1-(3,5-Dimethoxyphenyl)-1-(hex-1-enyl)-cyclopentane.

To the above slurry of (butylmethylene) triphenylphosphorane at 10° C. under an argon atmosphere was added dropwise a solution of (3,5-dimethoxyphenyl)cyclopentane carboxaldehyde (1 equiv.) in dry THF (0.21M). The reaction was stirred for 45 min and upon completion was quenched by the addition of saturated aqueous ammonium chloride. The organic layer was separated and the aqueous phase was extracted twice with diethyl ether. The combined organic layer was washed with brine, dried over $MgSO_4$ and the solvent was evaporated under reduced pressure to give an oil. The crude product was purified through a short column of silica gel using 5% diethyl ether-petroleum ether as eluent to afford the title compound in 96% yield.

1-(3,5-Dimethoxyphenyl)-1-hexyl-cyclopentane.

To a solution of 1-(3,5-dimethoxyphenyl)-1-(hex-1-enyl)-cyclopentane (1 equiv.) in ethyl acetate (0.11M) was added 10% Pd/C (17%, w/w) and the resulting suspension was stirred vigorously under an hydrogen atmosphere, overnight at room temperature. The catalyst was removed by filtration through celite and the filtrate was evaporated under reduced pressure to afford the crude product. Purification through a short column of silica gel using 5% diethyl ether-petroleum ether yielded the title compound in 95% yield.

5-(1-Hexyl-cyclopentyl)resorcinol, (compound 1a).

To a solution of 1-(3,5-dimethoxyphenyl)-1-hexyl-cyclopentane (1 equiv.) in dry methylene chloride (0.04M) at −78° C. under an argon atmosphere was added boron tribromide (2.5 equiv., 1M solution in methylene chloride). Following the addition, the reaction temperature was gradually raised over a period of 3 h to −20° C. Stirring was continued at that temperature until completion of the reaction. Unreacted boron tribromide was destroyed by addition of methanol and ice at 0° C. The resulting mixture was warmed at room temperature, stirred for 40 min and the solvent was removed in vacuo. The residual oil was diluted with ethyl acetate and the solution was washed with saturated sodium bicarbonate, water and brine. The organic layer was dried over $MgSO_4$, filtered and concentrated under reduced pressure. Purification by flash column chromatography (40% diethyl ether-petroleum ether as eluent) afforded the title compound in 90% yield.

$^1$H NMR (500 MHz, $CDCl_3$) δ: 6.36 (d, J=1.6 Hz, 2H), 6.19 (t, J=1.6 Hz, 1H), 5.78 (brs, 2H, OH), 1.83–1.77 (m, 2H), 1.73–1.58 (m, 6H), 1.51–1.48 (m, 2H), 1.22–1.12 (m, 6H), 1.02–0.94 (m, 2H), 0.83 (t, J=7.1 Hz, 3H).

5-[1-(Hex-1-enyl)-cyclopentyl]resorcinol, (compound 1b)

To a solution of 1-(3,5-dimethoxyphenyl)-1-(hex-1-enyl)-cyclopentane (1 equiv.) in dry hexane (0.05M) at 0° C. under an argon atmosphere was added 9-iodo-9-BBN (2.3 equiv., 1M solution in hexane). The mixture was stirred at the same temperature for 3.5 h and then the reaction temperature was raised to 27° C. Stirring was continued at that temperature until completion of the reaction. The volatiles were removed in vacuo, the residual oil was dissolved in diethyl ether, and a solution of ethanolamine (2.4 equiv.) in THF (1.4 M) was added causing spontaneous precipitation of the 9-BBN.ethanolamine adduct. The suspension was stirred for 2.5 h, the white precipitate was filtered off and the filtrate was evaporated under reduced pressure to give an oil. Purification by flash column chromatography on silica gel using 40% diethyl ether—petroleum ether as eluent afforded the title compound in 82% yield.

$^1$H NMR (500 MHz, $CDCl_3$) δ: 6.44 (d, J=1.9 Hz, 2H), 6.17 (t, J=1.9 Hz, 1H), 5.66 (d, J=11.0 Hz, 1H), 5.28 (dt, J=11.0 Hz, J=7.3 Hz, 1H), 5.14 (brs, 2H, OH), 2.01–1.85 (m, 4H), 1.80–1.65 (m, 6H), 1.15–1.07 (m, 4H), 0.77 (t, J=6.8 Hz, 3H).

Resorcinol compound 1c (shown in Scheme 3) was synthesized by the method disclosed in Papahatjis et al. *J. Med. Chem.*, 41: 1195–1200 (1998), the content of which is hereby incorporated by reference. Resorcinol compound 1 d (shown in Scheme 3) was synthesized by the method disclosed in Yan Guo et al. *J. Med. Chem.*, 37: 3867–3870 (1994), the content of which is hereby incorporated by reference.

Resorcinol compound 1e (shown in Scheme 2) was synthesized by the method depicted in Scheme 2.

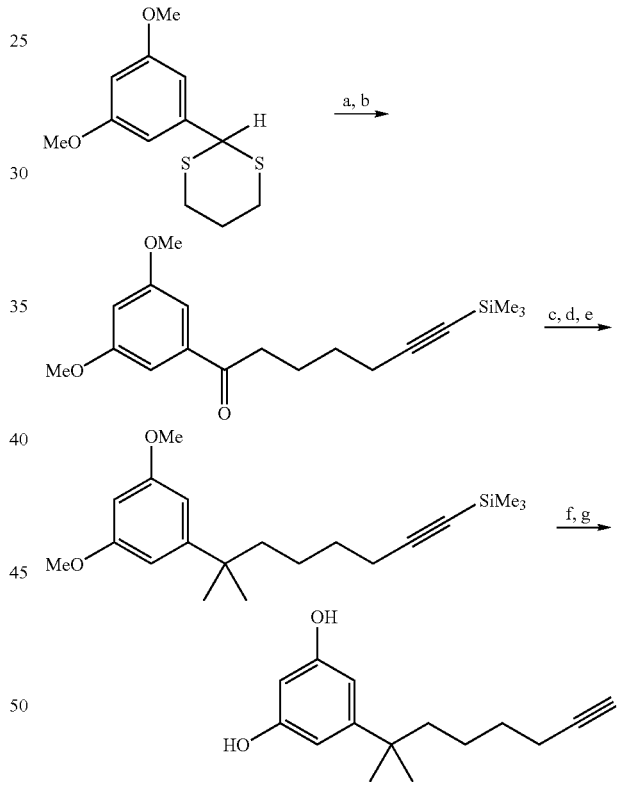

Scheme 2

Reagents and conditions. a) n-BuLi, -30° C., THF, $Br(CH_2)_4C\equiv CTMS$;
b) $(CF_3COO)_2IPh$, aq. MeOH; c) $CH_3MgBr$, $Et_2O$; d) $HCl_{(g)}$, $CCl_4$; e) $Me_3Al$,
-30° C. to r.t, toluene; f) $K_2CO_3$, MeOH; g) $BBr_3$, -40° C. to 0° C., $CH_2Cl_2$ General Procedure:
[7-(3,5-Dimethoxyphenyl-1,3-dithian-7-yl)-1-heptynyl] trimethylsilane.

A solution of 2-(3,5-dimethoxyphenyl)-1,3-dithiane (1 equiv.) in dry tetrahydrofuran (0.5 M) was cooled to −30° C. under argon and n-butyllithium (1.2 equiv., 1.6 M solution in hexanes) was added dropwise. The yellow-brown reaction mixture was stirred at the same temperature for 2 hours and (6-bromo-1-hexynyl)trimethylsilane (1.2 equiv.) was added in a dropwise manner when the color changed from yellow-brown to light yellow. The reaction mixture was allowed to warm to room temperature overnight and poured into water and extracted with diethyl ether. The combined organic extracts were dried and ether removed to give the crude product which was purified on silica gel (15% diethyl ether-petroleum ether) to afford the title compound in 86% yield as an oil.

Anal. calcd. for $C_{21}H_{32}O_2S_2Si$ C, 61.72; H, 7.89; found C, 61.49; H, 8.24.

[7-(3,5-Dimethoxyphenyl)-7-oxo-1-heptynyl]trimethylsilane.

A solution of [7-(3,5-dimethoxyphenyl-1,3-dithian-7-yl)-1-heptynyl]trimethylsilane (1 equiv.) in 10% aqueous methanol (0.1 M) was cooled in an ice-bath and bis(trifluoroacetoxy)iodobenzene (1.5 equiv.) was added portionwise with stirring. The reaction mixture was stirred for an additional 10 min and poured into sodium bicarbonate solution. The mixture was extracted with diethyl ether, ether extracts were combined, dried and solvent removed to afford an oil which was chromatographed on silica gel to afford the title compound in 90% yield.

Anal. calcd. for $C_{18}H_{26}O_3Si$ C, 67.88; H, 8.23; found C, 67.56; H, 8.55

[7-(3,5-Dimethoxyphenyl)-7-methyl-1-octynyl]trimethylsilane.

[7-(3,5-Dimethoxyphenyl)-7-oxo-1-heptynyl]trimethylsilane (1 equiv.) was dissolved in anhydrous ether (0.5 M), the solution was cooled in an ice-bath under argon and methylmagnesium bromide (2 equiv., 3M solution in diethyl ether) was added dropwise. The light gray solution was allowed to warm to room temperature and stirred for an additional hour. The reaction mixture was poured into saturated ammonium chloride solution, the organic phase was separated and the aqueous phase was extracted with diethyl ether. The combined organic extracts were dried and ether removed to afford pure [7-(3,5-dimethoxyphenyl)-7-hydroxy-1-octynyl]trimethylsilane as a viscous oil after passing through a short silica gel column, in 95% yield.

The above tertiary carbinol (1 equiv.) was dissolved in anhydrous carbon tetrachloride (0.5 M) and dry hydrogen chloride gas was bubbled through for 1 hour. The solution was transferred to a separatory funnel with the aid of more carbon tetrachloride, washed with water and 10% sodium bicarbonate solution. The organic phase was dried and rotary evaporated to afford an oil which was passed through a short silica gel column to give pure [7-chloro-7-(3,5-dimethoxyphenyl)-1-octynyl]trimethylsilane.

A solution of the above chloride (1 equiv.) in dry toluene was cooled to −30° C. under argon and trimethylaluminum (2 equiv., 2M solution in toluene) was added in a slow dropwise manner. The resulting clear reaction mixture was stirred at room temperature for about 16 hours and then 5% aqueous hydrochloric acid was added in a very cautious manner. The organic layer was separated, washed with water, dried and toluene removed. The residual oil was chromatographed on silica gel to afford the title compound as colorless oil.

$^1$H NMR (CDCl$_3$) δ 6.47 (d, J=2.16 Hz, 2H), 6.28 (t, J=2.16 Hz, 1H), 3.78 (s, 6H), 2.14 (t, J=7.08 Hz, 2H), 1.63–1.06 [overlapping patterns i.e., 1.63–1.06 (m, 6H), 1.25 (s, 6H)], 0.10 (s, 9H).

Anal. calcd. for $C_{20}H_{32}O_2Si$ C, 72.23; H, 9.70; found C, 71.98; H, 9.87.

7-(3,5-Dimethoxyphenyl)-7-methyl-1-octyne.

[7-(3,5-Dimethoxyphenyl)-7-methyl-1-octynyl]trimethylsilane (1 equiv.) was dissolved in anhydrous methanol (0.8 M), anhydrous potassium carbonate (0.2 equiv.). was added and the heterogeneous mixture was stirred at room temperature, under argon, for 24 hours. The reaction mixture was diluted with water and extracted with diethyl ether. The ether extract was dried, concentrated by rotary evaporation and the residue was purified by chromatography on silica gel (5% diethyl ether-petroleum ether) to give the title compound in 76% yield.

3-(1,1-Dimethylhept-6-ynyl)resorcinol, (compound 1e)

A solution of 7-(3,5-dimethoxyphenyl)-7-methyl-1-octyne (1 equiv.) in anhydrous dichloromethane (0.1 M) was cooled to −40° C. under argon and boron tribromide (2.5 equiv., 1M solution in dichloromethane) was added via syringe. The reaction mixture was allowed to warm to 0° C. with stirring over a period of 1–1.5 hours and then quenched with saturated sodium bicarbonate. The organic layer was separated, dried and solvent removed. The residue was chromatographed on silica gel (30–40% diethyl ether-petroleum ether) to give the title resorcinol in 56% yield.

$^{13}$C NMR (CDCl$_3$) δ 156.37, 153.11, 105.92, 100.11, 84.76, 68.22, 55.30, 43.77, 37.70, 29.03, 28.79, 23.87, 18.24.

2. Bicyclic Cannabinoid Synthesis

The bicyclic ketones (compound 2 with, for example, R groups a, b, c, d or e shown in Scheme 3) were synthesized by the method depicted in Scheme 3.

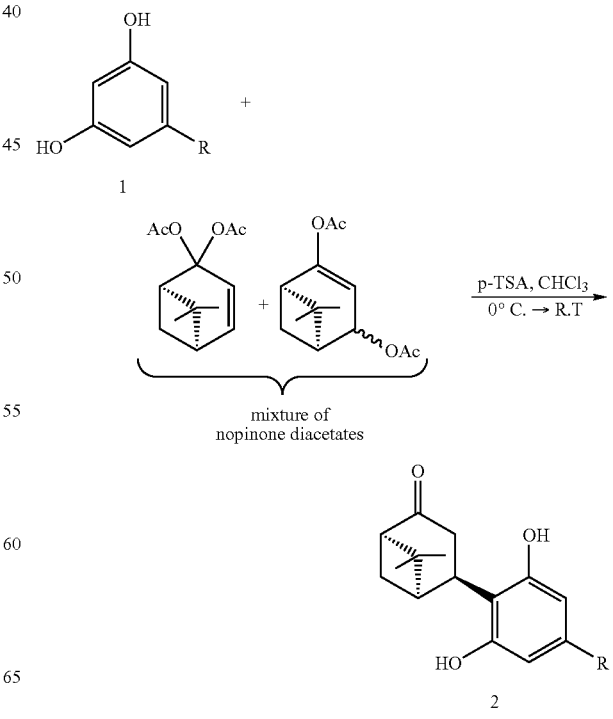

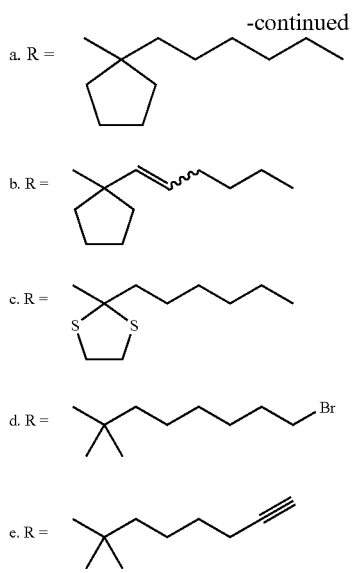

General Procedure:

To a solution of resorcinol (1 equiv.) and nopinone diacetates (approximately 1.3 equiv., ca. 87% pure by $^1$H NMR) in chloroform (approximately 0.1M) at 0° C. was added p-toluene sulfonic acid monohydrate (approximately 1.3 equiv.). Following the addition, the reaction temperature was raised to room temperature and stirring was continued for 4 hours to 3 days to ensure complete formation of the product. The reaction mixture was diluted with an organic solvent and washed sequentially with water, saturated aqueous sodium bicarbonate, and brine. The organic phase was dried over MgSO$_4$ and the solvent was removed under reduced pressure. The residue was chromatographed on silica gel to afford the bicyclic ketone.

Compound 2a (4R)-4-[4-(1',1'-cyclopentylheptyl)-2,6-dihydroxyphenyl]-6,6-dimethyl-2-norpinanone. Yield: 49%; white solid; mp=187–188° C.

Compound 2b (4R)-4-[4-(1',1'-cyclopentylhept-2'-enyl)-2,6-dihydroxyphenyl]-6,6-dimethyl-2-norpinanone. Yield: 47%; white solid; mp=167–168° C.

Compound 2c (4R)-4-[4-(2-hexyl-1,3-dithiolan-2-yl)-2,6-dihydroxyphenyl]-6,6-dimethyl-2-norpinanone. Yield: 13%; white solid; mp=160–161° C. dec.

$^1$H NMR (500 MHz, CDCl$_3$) δ: 6.68 (s, 2H, ArH), 5.02 (brs, 2H, OH), 3.95 (t, J=8.2 Hz, 1H), 3.44 (dd, J=18.7 Hz, J=7.8 Hz, 1H), 3.37–3.30 (m, 2H), 3.25–3.18 (m, 2H), 2.60 (dd, J=19.5 Hz, J=8.5 Hz, 1H), 2.58 (t, J=4.7 Hz, 1H), 2.53–2.49 (m, 1H), 2.44 (d, J=10.8 Hz, 1H), 2.30 (m, 1H), 2.26–2.22 (m, 2H), 1.36 (s, 3H), 1.27–1.19 (m, 8H), 0.99 (s, 3H), 0.85 (t, J=6.5 Hz, 3H).

Compound 2d (4R)-4-[4-(7'-bromo-1',1'-dimethylheptyl)-2,6-dihydroxyphenyl]-6,6-dimethyl-2-norpinanone. Yield: 41%; light yellow solid. The title compound (2d) was used in the preparation of the derivative compound 4d.

Anal. calcd. for $C_{24}H_{34}BrO_2$ C, 63.85; H, 7.81; found C, 63.99, H, 8.20.

Compound 2e (4R)-4-[4-(1',1'-dimethylhept-6'-ynyl)-2,6-dihydroxyphenyl]-6,6-dimethyl-2-norpinanone. Yield: 40%. The title compound (2e) was used in the preparation of the derivative compound 4e.

FAB HRMS calcd for $C_{24}H_{32}O_3$ 369.2430 (M+H$^+$); found 369.2430.

Compound 3

Synthesis of a diastereomeric mixture of (4R)-4-[4-(2-hexyl-1,3-dithiolan-2-yl)-2,6-dihydroxyphenyl]-6,6-dimethyl-2β-norpinanol and (4R)-4-[4-(2-hexyl-1,3-dithiolan-2-yl)-2,6-dihydroxyphenyl]-6,6-dimethyl-2α-norpinanol.

The title mixture (compound 3) was synthesized by the method depicted in Scheme 4 below.

Scheme 4

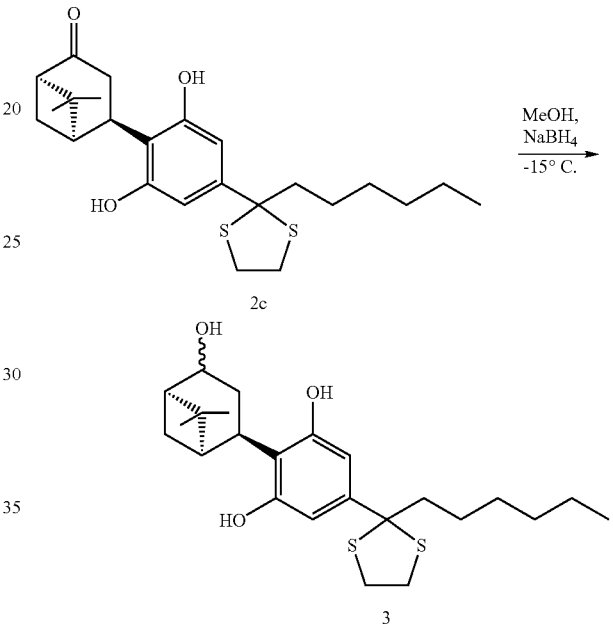

Procedure:

To a stirred solution of (4R)-4-[4-(2-hexyl-1,3-dithiolan-2-yl)-2,6-dihydroxyphenyl]-6,6-dimethyl-2-norpinanone (compound 2c) (11 mg, 0.025 mmol) in methanol (0.5 ml) at −15° C. under an argon atmosphere was added sodium borohydride (3 mg 0.079 mmol). The reaction was stirred at the same temperature for 2.5 hours and upon completion was quenched by the addition of saturated aqueous ammonium chloride. The volatiles were removed in vacuo and the residue was extracted with ethyl acetate. The organic layer was washed with water and brine, dried over MgSO$_4$ and the solvent evaporated. The residue was chromatographed on silica gel to afford 6 mg (54%) of the title mixture as a white glassy.

Preparation of Compounds of Compound Formula IV, V, VI 3. 9-Nor-9-oxohexahydrocannabinol synthesis The 9-Nor-9-oxohexahydrocannabinols (compound 4 with, for example, R groups a, b, c, d and e shown in Scheme 5) were synthesized by the method depicted in Scheme 5.

Scheme 5

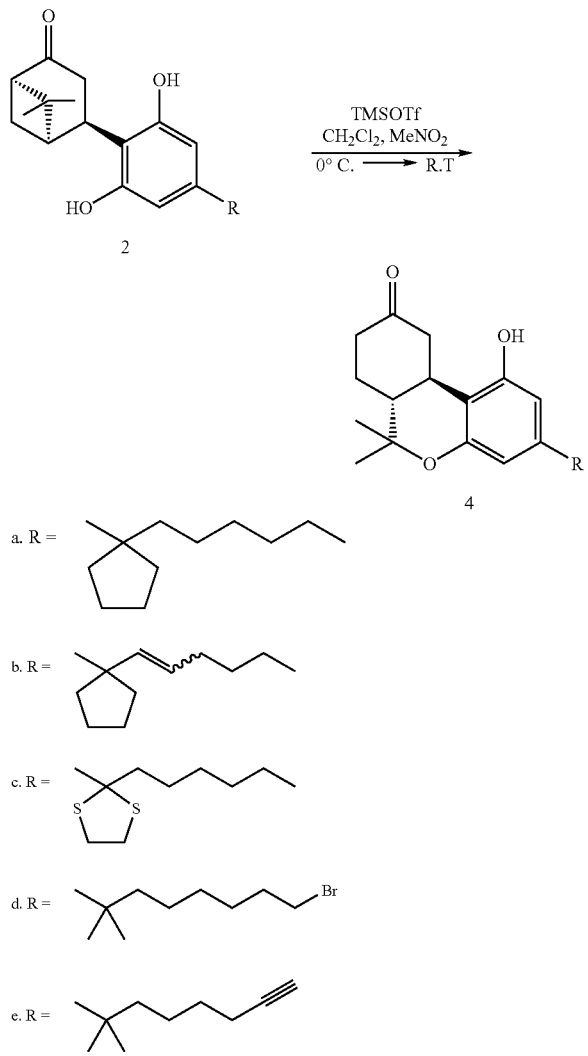

General Procedure:

To a stirred solution of bicyclic ketone (1 equiv.) in a mixture of dry methylene chloride-nitromethane (approximately 0.01–0.05M) at 0° C., under an argon atmosphere was added trimethylsilyl trifluoromethanesulfonate (approximately 0.3–1.3 equiv.). Following the addition, the mixture was stirred from 0° C. to room temperature for 1–7 hours. The reaction was quenched with saturated aqueous sodium bicarbonate/brine (1:1), and organic solvent was added. The organic phase was separated, the aqueous phase was extracted with organic solvent, and the combined organic phase was washed with brine and dried over MgSO$_4$. Solvent evaporation followed by flash column chromatography on silica gel afforded 9-Nor-9-oxohexahydrocannabinols.

Compound 4a (−)-trans-3-(1',1'-cyclopentylheptyl)-6,6a,7,8,10,10a-hexahydro-1-hydroxy-6,6-dimethyl-9H-dibenzo[b,d]pyran-9-one. Yield: 75%; White foam.

Compound 4b (−)-trans-3-(1',1'-cyclopentylhept-2'-enyl)-6,6a,7,8,10,10a-hexahydro-1-hydroxy-6,6-dimethyl-9H-dibenzo[b,d]pyran-9-one. Yield: 73%; White foam.

Compound 4c (−)-trans-3-(2-hexyl-1,3-dithiolan-2-yl)-6,6a,7,8,10,10a-hexahydro-1-hydroxy-6,6-dimethyl-9H-dibenzo[b,d]pyran-9-one. Yield: 83%; White foam; mp=62–64° C. dec.

$^1$H NMR (500 MHz, CDCl$_3$) δ: 6.76 (d, J=1.8 Hz, 1H, ArH), 6.64 (d, J=1.8 Hz, 1H, ArH), 5.85 (s, 1H, OH), 3.94 (d, J=14.6 Hz, 1H), 3.36–3.30 (m, 2H), 3.28–3.21 (m, 2H), 2.87 (td, J=11.9 Hz, J=3.3 Hz, 1H), 2.63–2.59 (m, 1H), 2.48–2.40 (m, 1H), 2.27 (m, 2H), 2.18–2.14 (m, 2H), 1.96 (td, J=11.7 Hz, J=2.0 Hz, 1H), 1.56–1.45 (m, 4H), 1.26–1.19 (m, 8H), 1.12 (s, 3H), 0.84 (t, J=7.0 Hz, 3H).

Compound 4d (−)-trans-3-(7'-bromo-1',1'-dimethylheptyl)-6,6a,7,8,10,10a-hexahydro-1-hydroxy-6,6-dimethyl-9H-dibenzo[b,d]pyran-9-one. Yield: 71%; light yellow foam. The title compound (4d) was used in the preparation of the derivative compound 6d.

Anal. calcd. for C$_{24}$H$_{34}$BrO$_2$ C, 63.85; H, 7.81; found C, 63.99; H, 8.20.

Compound 4e (−)-trans-3-(1',1'-dimethylhept-6'-ynyl)-6,6a,7,8,10,10a-hexahydro-1-hydroxy-6,6-dimethyl-9H-dibenzo[b,d]pyran-9-one. Following the general workup, the residue passed through a short column of silica gel and the title compound (4e) was used in the preparation of the derivative compound 6e without further purification.

4. 9-Nor-9β-hydroxyhexahydrocannabinol synthesis

Compound 5

6a,7,8,9,10,10a-Hexahydro-3-(2-hexyl-1,3-dithiolan-2-yl)-6,6-dimethyl-6H-dibenzo[b,d]pyran-1,9β-diol, was synthesized by the method depicted in Scheme 6.

Scheme 6

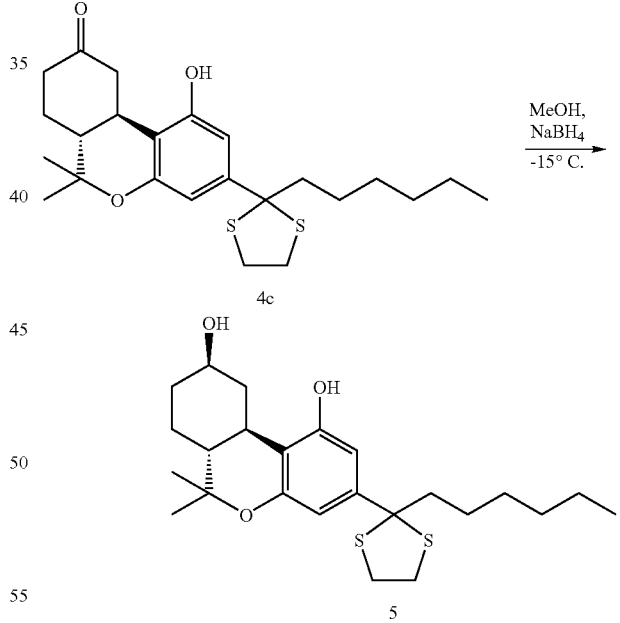

Procedure:

To a stirred solution of (−)-trans-3-(2-hexyl-1,3-dithiolan-2-yl)-6,6a,7,8,10,10a-hexahydro-1-hydroxy-6,6-dimethyl-9H-dibenzo[b,d]pyran-9-one (compound 4c) (1 equiv.) in methanol (approximately 0.05M) at −15° C. under an argon atmosphere was added sodium borohydride (approximately 5 equiv.). The reaction was stirred at the same temperature and upon completion was quenched by the addition of saturated aqueous ammonium chloride. The volatiles were removed in vacuo and the residue was extracted with ethyl acetate. The organic layer was washed with water and brine, dried over MgSO₄ and the solvent evaporated. The residue was chromatographed on silica gel to afford the title compound in 69% yield.

$^1$H NMR (CDCl$_3$) δ: 6.70 (d, J=1.7 Hz, 1H, ArH), 6.59 (d, J=1.7 Hz, 1H, ArH), 5.98 (brs, 1H), 3.89–3.84 (m, 1H, H-9), 3.51–3.49 (m, 1H), 3.34–3.21 (m, 4H), 2.47 (t, J=10.81 Hz, 1H), 2.30–1.37 (11H, especially 1.38, s Me), 1.26–1.16 (m, 8H), 1.06 (s, 3H, Me), 0.84 (t, J=6.9 Hz, 3H).

5. 9-Nor-9α-hydroxyhexahydrocannabinol synthesis

The 9-Nor-9α-hydroxyhexahydrocannabinols (compound 6 with, for example, R groups d and e shown in Scheme 7) were synthesized by a method depicted in Scheme 7 below.

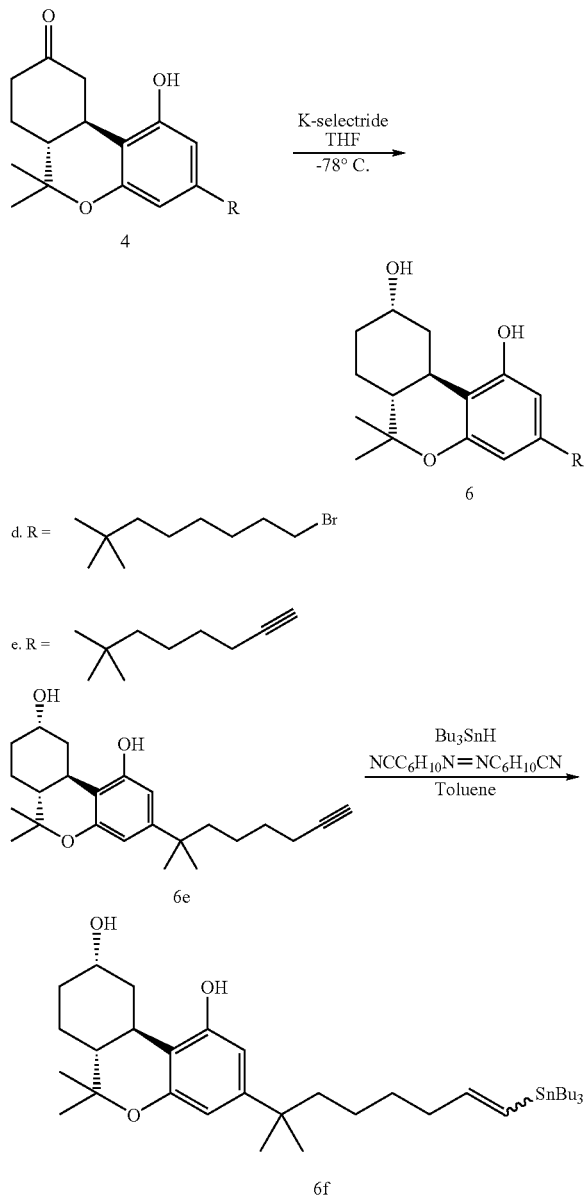

General Procedure:

A solution of 9-nor-9-oxohexahydrocannabinol (1 equiv.) in anhydrous THF (approximately 0.02M) was cooled to −78° C. under argon and a 1 M solution of K-selectride in THF (approximately 5 equiv.) was added in a slow, dropwise manner. The reaction mixture was stirred at −78° C. for 2–5 hours and then quenched by cautious addition of water. The mixture was warmed to room temperature poured into 10% hydrochloric acid and the organic layer was separated. The aqueous layer was extracted the combined organic layer dried (MgSO₄) and solvent evaporated. The residue was chromatographed on silica gel to afford 9-Nor-9α-hydroxyhexahydrocannabinols.

Compound 6d 6a,7,8,9,10,10a-Hexahydro-3-(7'-bromo-1',1'-dimethylheptyl)-6,6-dimethyl-6H-dibenzo[b,d]pyran-1,9α-diol. Yield: 60%. The title compound (6d) was used in the preparation of the derivative compound 7d.

Compound 6e 6a,7,8,9,10,10a-Hexahydro-3-(1',1'-dimethylhept-6'-ynyl)-6,6-dimethyl-6H-dibenzo[b,d]pyran-1,9α-diol. The title compound (6e) was used in the preparation of the derivative compound 6f.

FAB HRMS calcd for C$_{24}$H$_{34}$O$_3$ 371.2589 (M+H$^+$); found 371.2588.

Compound 6f 6a,7,8,9,10,10a-Hexahydro-3-(7'-tri-n-butyltin-1',1'-dimethylhept-6'-enyl)-6,6-dimethyl-6H-dibenzo[b,d]pyran-1,9α-diol.

Procedure:

A mixture of 3-(1',1'-dimethylhept-6'-ynyl)-9α-hydroxyhexahydrocannabinol (compound 6e) (100 mg, 0.27 mmol), 1,1'-azobis (cyclohexanecarbonitrile) (20 mg) and 0.16 mL of tri-n-butyltin hydride in 5.3 mL of dry toluene was refluxed for 10 h under argon. The mixture was cooled to room temperature, toluene was removed in vacuo and the residue was chromatographed on silica gel (30–50% ethyl ether-petroleum ether) to afford 130 mg (73%) of the title compound (6f) as a colorless oil.

FAB HRMS calcd for C$_{38}$H$_{63}$O$_3$Sn 663.3799 (M+H$^+$); found 663.3798.

6. 9-Nor-9β-azidohexahydrocannabinol synthesis

The 9-Nor-9β-azidohexahydrocannabinols (compound 7 with, for example, R groups d, f and g shown in Scheme 8) were synthesized by the method depicted in Scheme 8.

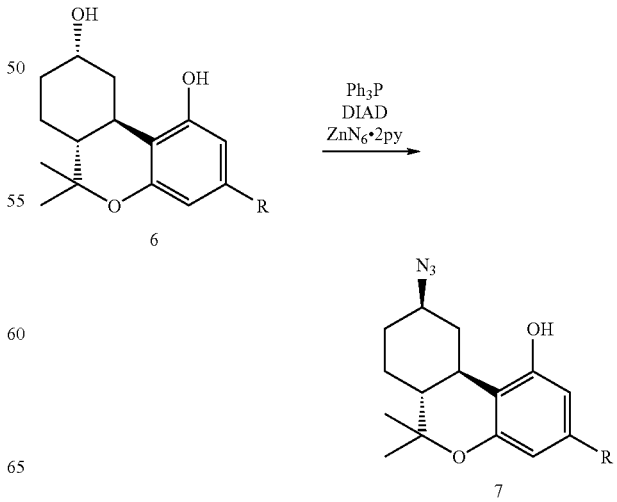

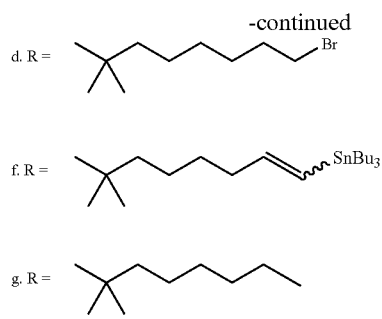

General Procedure:

A mixture of 9-Nor-9α-hydroxyhexahydrocannabinol (1 equiv.), zinc azide bipyridyl complex (approximately 1.5 equiv), triphenylphosphine (approximately, 4 equiv.) anhydrous organic solvent (approximately 0.25M) was stirred under argon and a solution of diisopropyl azodicarboxylate (DIAD, approximately 4 equiv.) in dry organic solvent was added in slow dropwise manner. The mixture was allowed to stir at room temperature and upon completion chromatographed on a silica gel column to afford the 9-Nor-9β-azidohexahydrocannabinols.

Compound 7d

1-Hydroxy-3-(7'-bromo-1',1'-dimethylheptyl)-6,6-dimethyl-9β-azido-6a,7,8,8,10,10a-hexahydro-6H-dibenzo[b,d]pyran. Yield 71%; The title compound (7d) was used in the preparation of the compound 8.

Compound 7f

1-Hydroxy-3-(7'-tri-n-butyltin-1',1'-dimethylhept-6'-enyl)-6,6-dimethyl-9β-azido-6a,7,8,8,10,10a-hexahydro-6H-dibenzo[b,d]pyran. Yield 72%; The title compound (7f) was used in the preparation of the compound 9.

Compound 7g

1-Hydroxy-3-(1',1'-dimethylheptyl)-6,6-dimethyl-9β-azido-6a,7,8,8,10,10a-hexahydro-6H-dibenzo[b,d]pyran. Yield 75%. The precursor for the title compound was synthesized by the method previously described for compound 6.

IR (AgCl): v=2096 cm$^{-1}$ (N$_3$).

The 9-Nor-9β-azidohexahydrocannabinols (compounds 8 and 9 shown in Scheme 9) were synthesized by the method depicted in Scheme 9.

Scheme 9

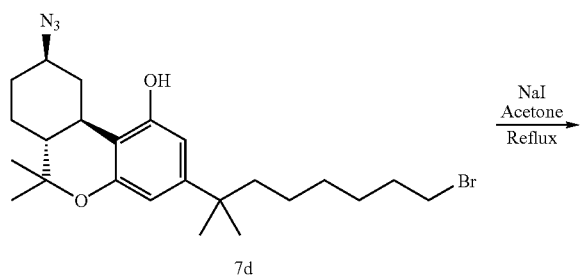

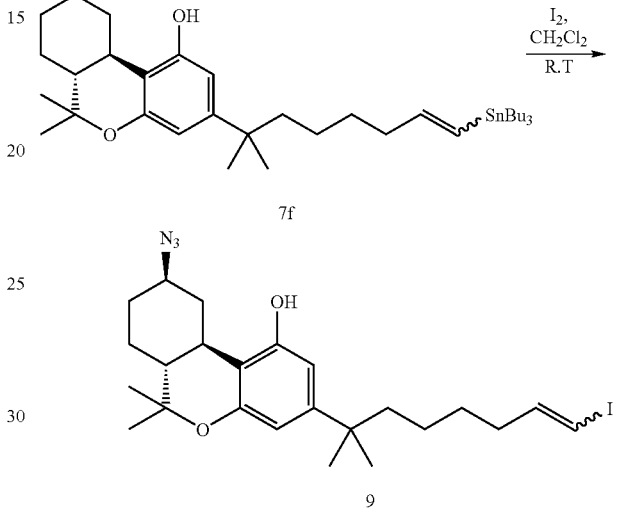

Compound 8

1-Hydroxy-3-(7'-iodo-1',1'-dimethylheptyl)-6,6-dimethyl-9β-azido-6a,7,8,8,10,10a-hexahydro-6H-dibenzo[b,d]pyran. The title compound (8) was synthesized by the method depicted in Scheme 9.

Procedure:

100 mg (0.21 mmol) of 9β-azido-3-(7'-bromo-1',1'-dimethylheptyl) hexahydrocannabinol (compound 7d) was dissolved in 5 ml of dry acetone, 63 mg (0.42 mmol) of sodium iodide was added and the solution was refluxed for 6 hours. Acetone was removed by rotary evaporation and the residue was extracted in ether. The ether extract was concentrated and the residue chromatographed to afford 88 mg (80%) of the title compound (8) as a gum.

Compound 9

1-Hydroxy-3-(7'-iodo-1',1'-dimethylhept-6'-enyl)-6,6-dimethyl-9β-azido-6a,7,8,8,10,10a-hexahydro-6H-dibenzo[b,d]pyran. The title compound (9) was synthesized by a method depicted in Scheme 9.

Procedure:

16 mg (0.023 mmol) of 9-Nor-9β-azidohexahydrocannabinol (compound 7f) was dissolved in 1 mL of dichloromethane and a solution of 8.7 mg (0.034 mmol) of iodine in 0.5 mL of dichloromethane was added dropwise. The solution was stirred at room temperature for 15 min and excess iodine was destroyed by adding a 0.1 M aqueous solution of sodium hydrogen sulfite. The organic layer was separated, dried (MgSO$_4$) and solvent removed. The residue was purified by column chromatography on silica gel to afford 12.8 mg of the title compound (9).

FAB HRMS calc'd for C$_{24}$H$_{34}$IN$_3$O$_2$ 524.1744 (M+H$^+$); found 524.1771.

Generally, the synthesis of compounds 2a–2e, 3, 4a–4e, 5, 6d–6f, 7d–7g, 8 and 9 was accomplished by the stereospecific condensation (Scheme 3, Scheme 5) of nopinone diacetates with an appropriately substituted resorcinol. On the other hand the requisite mixture of nopinone diacetates was prepared by the method disclosed in Drake et al. *J. Med. Chem.*, 3596 (1998). This method involves isopropenyl acetate based transesterification followed by lead tetraacetate oxidation with no loss of optical purity starting from commercially available (1R,5S)-(+)-nopinone. Since (1S, 5R)-(−)-nopinone of respectable optical purity can be obtained from commercially available (+)-β-pinene or (+)-α-pinene by the method disclosed in Brown et al. *J. Org. Chem.*, 1217 (1990) and in Lavalle'e et al. *J. Org. Chem.*, 1362 (1986) respectively, the enantiomers of the above mentioned compounds could be synthesized following the same methodology. Each of the above references is incorporated by reference herein.

The inventive analogs described herein, and physiologically acceptable salts thereof, have high potential when administered in therapeutically effective amounts for providing a physiological effect useful to treat pain; peripheral pain; glaucoma; epilepsy; nausea such as associated with cancer chemotherapy; AIDS Wasting Syndrome; cancer; neurodegenerative diseases including Multiple Sclerosis, Parkinson's Disease, Huntington's Chorea and Alzheimer's Disease; to enhance appetite; to reduce fertility; to prevent or reduce diseases associated with motor function such as Tourette's syndrome; to provide neuroprotection; to produce peripheral vasodilation and to suppress memory. Thus, another aspect of the invention is the administration of a therapeutically effective amount of an inventive compound, or a physiologically acceptable salt thereof, to an individual or animal to provide a physiological effect.

Those skilled in the art will recognize, or be able to ascertain with no more than routine experimentation, many equivalents to the specific embodiments of the invention disclosed herein. Such equivalents are intended to be encompassed by the scope of the invention.

What is claimed is:

1. A compound of formula I below, and physiologically acceptable salts thereof:

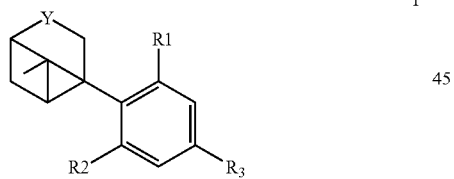

I wherein Y is selected from >C=O, >CH—(CH$_2$)$_f$—Y$_1$—(CH$_2$)$_g$—Y$_2$, >C=N—Y$_3$, >CH—NY$_4$Y$_5$, >CH—(CH$_2$)$_h$—Y$_6$, —C(O)N(Y$_7$)—, —N(Y$_7$)C(O)—, >NY$_{11}$, >N—(CH$_2$)$_f$—Y$_1$—(CH$_2$)$_g$—Y$_2$, a spirocycle, or CY$_9$Y$_{10}$, including all isomers, Y$_1$ is independently selected from O, CO, C(O)O, OCO or CH$_2$;

Y$_2$ is independently selected from H, halogen, CN, CF$_3$, N$_3$, OH, COOH, alkoxy, acyloxy, NCS, NCO or NY$_7$Y$_8$;

Y$_3$ is independently selected from —OH, —NH$_2$, alkoxy, alkyl, —(CH$_2$)$_n$—NR$_{10}$R$_{11}$, —(CH$_2$)$_n$—CO$_2$R where R is independently selected from H, alkyl, —O—(CH$_2$)$_n$—NR$_{10}$R$_{11}$, —O—(CH$_2$)$_n$—CO$_2$R or —O—(CH$_2$)$_n$—CONR$_{10}$R$_{11}$;

Y$_4$ is independently selected from H, OH, alkoxy or alkyl;

Y$_5$ is independently selected from H, OH, alkoxy or alkyl, wherein Y$_4$ and Y$_5$ cannot both be OH and wherein Y$_4$ and Y$_5$ cannot both be alkoxy;

Y$_6$ is independently selected from H, halogen, CN, COOH, COalkyl, CF$_3$, SO$_2$alkyl, COfluoroalkyl, N$_3$, OH, alkoxy, acyloxy, NCS, NCO or NY$_7$Y$_8$;

Y$_7$ is independently selected from H, alkyl, hydroxyalkyl, an aromatic ring, an aromatic ring substituted by at least one member selected from alkyl, alkoxy, halogen and CF$_3$, a heterocyclic ring or a heteroaromatic ring;

Y$_8$ is independently selected from H, alkyl, hydroxyalkyl, an aromatic ring, an aromatic ring substituted by at least one member selected from alkyl, alkoxy, halogen and CF$_3$, a heterocyclic ring or a heteroaromatic ring; or alternatively, Y$_7$ and Y$_8$ taken together comprise part at a 3 to 7 membered saturated heterocyclic ring containing up to one additional heteroatom selected from N, O and S;

Y$_9$ is independently selected from H, alkyl or alkoxycarbonylmethyl;

Y$_{10}$ is independently selected from H, alkyl or alkoxycarbonylmethyl;

Y$_{11}$ is independently selected from H, alkyl, CO, CN, CO-alkyl, SO$_2$-akyl or CF$_3$;

f is an integer from 0 to about 5;

g is an integer from 0 to about 5;

h is an integer from 0 to about 5;

n is an integer from 0 to about 4; and

R$_1$ and R$_2$ are each independently selected from H, OH, halogen, alkyl, —O-alkyl, NH$_2$, NO$_2$, CN, acyl, aroyl, benzoyl, substituted benzoyl, arylalkyl, substituted arylalkyl, phenacyl, substituted phenacyl, —O-alkyl-NR$_{10}$R$_{11}$, —O-alkyl-COOR where R is selected from H$_z$alkyl, —O-alkyl-CONR$_{10}$R$_{11}$, OCOCH$_3$, —N(alkyl)$_2$, —CO(alkyl)X or —OCO(alkyl)X where X is selected from H, dialkylamino, a cyclic amine, a carbocyclic ring, a heterocyclic ring, an aromatic ring or a heteroaromatic; and R$_{10}$ and R$_{11}$ are each independently selected from H, alkyl, hydroxyalkyl or R$_{10}$ and R$_{11}$ together comprise part of a 3 to 7 membered saturated heterocyclic ring containing up to one additional heteroatom selected from N, O and S and R$_3$ is selected from:

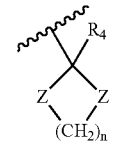

wherein each Z is independently selected from S, O, NH, N(CH$_3$), SO, SO$_2$ or CR$_{12}$R$_{13}$ where R$_{12}$ and R$_{13}$ are each independently selected from H or alkyl;

R$_4$ is selected from —(CH$_2$)$_j$—R$_5$, —(CH$_2$)$_j$-A-(CH$_2$)$_k$—R$_5$ or —(CH$_2$)$_j$-A-(CH$_2$)$_k$B—R$_5$;

A and B are each independently selected from —CH$_2$—CH$_2$—, —CH=CH—, —C≡C—, O, S, SO, SO$_2$ or NH;

R$_5$ is selected from H, halogen, CN, CF$_3$, N$_3$, COOH, NH$_2$, N(CH$_3$)$_2$, ⊕N(CH$_3$)$_3$, Sn(alkyl)$_3$, phenyl, COOR where R is selected from H or alkyl, a carbocylic ring, a heterocyclic ring, an aromatic ring, a heteroaromatic ring, a polycarbocyclic ring structure having 2 to about 5 rings, a polyheterocyclic ring structure having 2 to about 5 rings or $CONR_{10}R_{11}$, where $R_{10}$ and $R_{11}$ are each independently selected from H, alkyl, hydroxyalkyl or $R_{10}$ and $R_{11}$ together comprise part of a 5 or 6 membered saturated heterocyclic ring containing up to one additional heteroatom selected from N, O and S;

n is an integer from 1 to about 4;

j is an integer from 0 to about 7; and k is an integer from 0 to about 7; or $R_3$ is selected from:

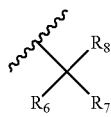

wherein $R_5$ and $R_7$ are each independently selected from H or alkyl;

$R_8$ is $-(CH_2)_j-C\equiv C-(CH_2)_k-R_9$;

$R_9$ is selected from H, halogen, CN, $CF_3$, $N_3$, COOH, $NH_2$, $N(CH_3)_2$, $\oplus N(CH_3)_3$, $Sn(alkyl)_3$, phenyl, COOR where R is selected from H or alkyl, a carbocylic ring, a heterocyclic ring, an aromatic ring, a heteroaromatic ring, a polycarbocyclic ring structure having 2 to about 5 rings, a polyheterocyclic ring structure having 2 to about 5 rings or $CONR_{10}R_{11}$ where $R_{10}$ and $R_{11}$ are each independently selected from H, alkyl, hydroxyalkyl or $R_{10}$ and $R_{11}$ together comprise part of a 5 or 6 membered saturated heterocyclic ring containing up to one additional heteroatom selected from N, O and S;

j is an integer from 0 to about 7; and k is an integer from 0 to about 7; or $R_1$ and $R_2$ are each independently selected from H, OH, alkyl or alkoxy and $R_3$ is:

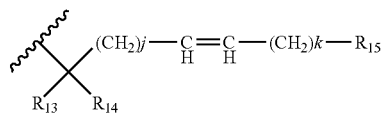

wherein $R_{13}$ and $R_{14}$ are each independently selected from H or alkyl;

$R_{15}$ is selected from H, halogen, CN, $CF_3$, $N_3$, COOH, $NH_2$, $N(CH_3)_2$, $\oplus N(CH_3)_3$, $Sn(alkyl)_3$, phenyl, COOR where R is selected from H or alkyl, a carbocylic ring, a heterocyclic ring, an aromatic ring, a heteroaromatic ring, a polycarbocyclic ring structure having 2 to about 5 rings, a polyheterocyclic ring structure having 2 to about 5 rings, or $CONR_{10}R_{11}$ where $R_{10}$ and $R_{11}$ are each independently selected from H, alkyl, hydroxyalkyl or $R_{10}$ and $R_{11}$ together comprise part of a 5 or 6 membered saturated heterocyclic ring containing up to one additional heteroatom selected from N, O and S;

j is an integer from 0 to about 7; and k is an integer from 0 to about 7; or

Y is $>CH-(CH_2)_h-Y_6$;

$Y_6$ is selected from CN or $N_3$ and h is an integer from about 1 to about 3, or $Y_5$ is selected from $N_3$ and h is an integer from 0 to about 3;

$R_1$ and $R_2$ are each independently selected from H, OH, alkyl or alkoxy; and $R_3$ is:

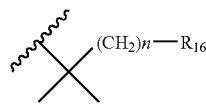

wherein $R_{16}$ is selected from H, halogen, CN, $CF_3$, $N_3$, COOH, $NH_2$, $N(CH_3)_2$, $\oplus N(CH_3)_3$, $Sn(alkyl)_3$, phenyl, COOR where R is selected from H or alkyl, a carbocylic ring, a heterocyclic ring, an aromatic ring, a heteroaromatic ring, a polycarbocyclic ring structure having 2 to about 5 rings, a polyheterocyclic ring structure having 2 to about 5 rings or $CONR_{10}R_{11}$ where $R_{10}$ and $R_{11}$ are each independently selected from H, alkyl, hydroxyalkyl or $R_{10}$ and $R_{11}$ together comprise part of a 5 or 6 membered saturated heterocyclic ring containing up to one additional heteroatom selected from N, O and S; and n is an integer from 0 to about 7; with the provisos that:

if Y is C=O, and $R_1$ is selected from H, OH, $OCH_3$, $NH_2$ and $O(CH_2)_nN(CH_3)_2$ where n is an integer from 1–3, and $R_2$ is selected from H, OH, and $OCH_3$, then $R_3$ cannot be selected from $(CH_2)_nC\equiv CH$ where n is an integer from 3–5, and

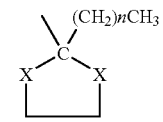

where each X is independently selected from $CH_2$, O, S and NH and n is an integer from 3–5; and if Y is C=O, and $R_1$ and $R_2$ are both OH, then $R_3$ cannot be $C(CH_3)_2(CH_2)_nCH_3$, where n is an integer from 3–5; and if Y is C=O, and one of $R_1$ or $R_2$ is H and the other of $R_1$ or $R_2$ is OCH3, then $R_3$ cannot be $(CH_2)_nCH_3$, where n is an integer from 4–6; and if Y is C=O, and $R_1$ and $R_2$ are both OH, then $R_3$ cannot be $(CH_2)_nCH_3$, where n is an integer from 4–6.

2. The compound of claim 1 wherein $R_3$ is:

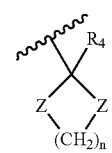

wherein each Z is independently selected from S, O, NH, $N(CH_3)$, SO, $SO_2$ or $CR_{12}R_{13}$ where $R_{12}$ and $R_{13}$ are each independently selected from H or alkyl;

$R_4$ is selected from $-(CH_2)_j-R_5$, $-(CH_2)_y-A-(CH_2)_k-R_5$ or $-(CH_2)_j-A-(CH_2)_k-B-R_5$;

A and B are each independently selected from $-CH_2-CH_2-$, $-CH=CH-$, $-C\equiv C-$, O, S, SO, $SO_2$ or NH;

$R_5$ is selected from H, halogen, CN, $CF_3$, $N_3$, COOH, $NH_2$, $N(CH_3)_2$, $\oplus N(CH_3)_3$, $Sn(alkyl)_3$, phenyl, COOR where R is selected from H or alkyl, a carbocylic ring, a heterocyclic ring, an aromatic ring, a heteroaromatic ring, a polycarbocyclic ring structure having 2 to about 5 rings, a polyheterocyclic ring structure having 2 to about 5 rings or CONR$_{10}$R$_{11}$ where R$_{10}$ and R$_{11}$ are each independently selected from H, alkyl, hydroxyalkyl or R$_{10}$ and R$_{11}$ together comprise pert of a 5 or 6 membered saturated heterocyclic ring containing up to one additional heteroatom selected from N, O and S;

n is an integer from 1 to about 4;

j is an integer from 0 to about 7; and k is an integer from 0 to about 7.

3. The compound of claim 1 wherein R$_3$ is:

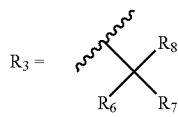

wherein R$_6$ and R$_7$ are each independently selected from H or alkyl;

R$_8$ is selected from —(CH$_2$)$_j$—C≡C—(CH$_2$)$_k$—R$_9$;
R$_9$ is selected from H, halogen, CN, CF$_3$, N$_3$, COOH, NH$_2$, N(CH$_3$)$_2$, ⊕N(CH$_3$)$_3$, Sn(alkyl)$_3$, phenyl, COOR where R is selected from H or alkyl, a carbocyclic ring, a heterocyclic ring, an aromatic ring, a heteroaromatic ring, a polycarbocyclic ring structure having 2 to about 5 rings, a polyheterocyclic ring structure having 2 to about 5 rings or CONR$_{10}$R$_{11}$, where R$_{10}$ and R$_{11}$ are each independently selected from H, alkyl, hydroxyalkyl or R$_{10}$ and R$_{11}$ together comprise part of a 5 or 6 membered saturated heterocyclic ring containing up to one additional heteroatom selected from N, O and S;
j is an integer from 0 to about 7; and
k is an integer from 0 to about 7.

4. The compound of claim 1, wherein R$_1$ and R$_2$ are each independently selected from H, OH, alkyl or alkoxy and R$_3$ is selected from:

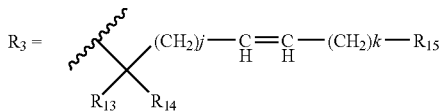

wherein R$_{13}$ and R$_{14}$ and are each independently from H or alkyl;

R$_{15}$ is selected from H, halogen, CN, CF$_3$, N$_3$, COOH, NH$_2$, N(CH$_3$)$_2$, ⊕N(CH$_3$)$_3$, Sn(alkyl)$_3$, phenyl, COOR where R is selected from H or alkyl, a carbocyclic ring, a heterocyclic ring, an aromatic ring, a heteroaromatic ring, a polycarbocyclic ring structure having 2 to about 5 rings, a polyheterocyclic ring structure having 2 to about 5 rings, or CONR$_{10}$R$_{11}$ where R$_{10}$ and R$_{11}$ are each independently selected from H, alkyl, hydroxyalkyl or R$_{10}$ and R$_{11}$ together comprise part of a 5 or 6 membered saturated heterocyclic ring containing up to one additional heteroatom selected from N, O and S;

j is an integer from 0 to about 7; and k is an integer from 0 to about 7.

5. The compound of claim 1 wherein Y is >CH—(CH$_2$)$_h$—Y$_6$;
Y$_6$ is selected from CN or N$_3$ and h is an integer from about 1 to about 3, or Y$_6$ is N$_3$ and h is an integer from 0 to about 3;
R$_1$ and R$_2$ each comprise H, OH, alkyl or alkoxy;

R$_3$ is:

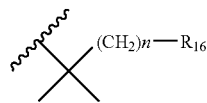

wherein R$_{15}$ is selected from H, halogen, CN, CF$_3$, N$_3$, COOH, NH$_2$, N(CH$_3$)$_2$, ⊕N(CH$_3$)$_3$, Sn(alkyl)$_3$, phenyl, COOR where R is selected from H or alkyl, a carbocyclic ring, a heterocyclic ring, an aromatic ring, a heteroaromatic ring, a polycarbocyclic ring structure having 2 to about 5 rings, a polyheterocyclic ring structure having 2 to about 5 rings or CONR$_{10}$R$_{11}$ where R$_{10}$ and R$_{11}$ are each independently selected from H, alkyl, hydroxyalkyl or R$_{10}$ and R$_{11}$ together comprise part of a 5 or 6 membered saturated heterocyclic ring containing up to one additional heteroatom selected from N, O and S; and n is an integer from 0 to about 7.

6. A compound of formula IV below, and physiologically acceptable salts thereof:

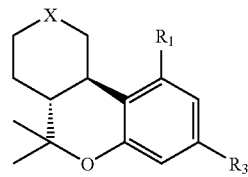

wherein X is selected from >C=O, >CH—(CH$_2$)$_f$—X$_1$—(CH$_2$)$_g$—X$_2$, >C=N—X$_3$, >CH—NX$_4$X$_5$, >CH—(CH$_2$)$_h$—X$_6$, —C(O)N(X$_7$)—, —N(X$_7$)C(O)—, >NX$_{11}$, >N—(CH$_2$)$_f$—X$_1$—(CH$_2$)$_g$—X$_2$, a spirocycle, or CX$_9$X$_{10}$, including all isomers;

X$_1$ is independently selected from O, CO, C(O)O, OCO or CH$_2$;

X$_2$ is independently selected from H, halogen, CN, CF$_3$, N$_3$, OH, COOH, alkoxy, acyloxy, NCS, NCO or NX$_7$X$_8$;

X$_3$ is independently selected from —OH, —NH$_2$, alkoxy, alkyl, —(CH$_2$)$_n$—NR$_{10}$R$_{11}$, —(CH$_2$)$_n$—CO$_2$R where R is selected from H or alkyl, —O—(CH$_2$)$_n$—NR$_{10}$R$_{11}$, —O—(CH$_2$)$_n$—CO$_2$R or —O—(CH$_2$)$_n$—CONR$_{10}$R$_{11}$;

X$_4$ is independently selected from H, OH, alkoxy or alkyl;

X$_5$ is independently selected from H, OH, alkoxy or alkyl, wherein X$_4$ and X$_5$ cannot both be OH and wherein X$_4$ and X$_5$ cannot both be alkoxy;

X$_6$ is independently selected from H, halogen, CN, COOH, COalkyl, CF$_3$, SO$_2$alkyl, COfluoroalkyl, N$_3$, OH, alkoxy, acyloxy, NCS, NCO or NX$_7$X$_8$;

X$_7$ is independently selected from H, alkyl, hydroxyalkyl, an aromatic ring, an aromatic ring substituted by at least one member selected from alkyl, alkoxy, halogen and CF$_3$, a heterocyclic ring or a heteroaromatic ring;

X$_8$ is independently selected from H, alkyl, hydroxyalkyl, an aromatic ring, an aromatic ring substituted by at least one member selected from alkyl, alkoxy, halogen and CF$_3$, a heterocyclic ring or a heteroaromatic ring; or alternatively, X$_7$ and X$_8$ taken together comprise part of a 3 to 7 membered saturated heterocyclic ring containing up to one additional heteroatom selected from N, O and S;

$X_9$ is independently selected from H, alkyl or alkoxycarbonylmethyl;

$X_{10}$ is independently selected from H, alkyl or alkoxycarbonylmethyl;

$X_{11}$ is independently selected from H, alkyl, CO, CN, COalkyl, $SO_2$alkyl or $CF_3$;

f is an integer from 0 to about 3;

g is an integer from 0 to about 3;

h is an integer from 0 to about 3;

n is an integer from 0 to about 4;

$R_1$ is independently selected from H, OH, halogen, alkyl, —O-alkyl, $NH_2$, $NO_2$, CN, acyl, aroyl, benzoyl, substituted benzoyl, arylalkyl, substituted arylalkyl, phenacyl, substituted phenacyl, —O-alkyl-$NR_{10}R_{11}$, —O-alkyl-COOR where R selected from H or alkyl, —O-alkyl-$CONR_{10}R_{11}$, $OCOCH_3$, —N(alkyl)$_2$, —CO(alkyl)X or —OCO(alkyl)X where X is selected from H, dialkylamino, a cyclic amine, a carbocyclic ring, a heterocyclic ring, an aromatic ring or a heteroaromatic; and $R_{10}$ and $R_{11}$ each independently selected from H, alkyl, hydroxyalkyl or $R_{10}$ and $R_{11}$ together comprise part of a 3 to 7 membered saturated heterocyclic ring containing up to one additional heteroatom selected from N, O and S; and $R_3$ is selected from:

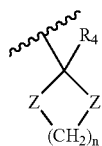

wherein each Z independently selected from S, O, NH, N(CH$_3$), SO, SO$_2$ or $CR_{12}R_{13}$ where $R_{12}$ and $R_{13}$ are each independently selected from H or alkyl;

$R_4$ is selected from —(CH$_2$)$_j$—R$_5$, —(CH$_2$)$_j$-A-(CH$_2$)$_k$—R$_5$ or —(CH$_2$)$_j$-A-(CH$_2$)$_k$—B—R$_5$, A and B each independently selected from —CH$_2$—CH$_2$—, —CH=CH—, —C≡C—, O, S, SO, SO$_2$ or NH;

$R_5$ is selected from H, halogen, CN, CF$_3$, N$_3$, COOH, NH$_2$, N(CH$_3$)$_2$, ⊕N(CH$_3$)$_3$, Sn(alkyl)$_3$, phenyl, COOR where R is selected from H or alkyl, a carbocyclic ring, a heterocyclic ring, an aromatic ring, a heteroaromatic ring, a polycarbocyclic ring structure having 2 to about 5 rings, a polyheterocyclic ring structure having 2 to about 5 rings or $CONR_{10}R_{11}$ where $R_{10}$ and $R_{11}$ are each independently selected from H, alkyl, hydroxyalkyl or $R_{10}$ and $R_{11}$ together comprise part of a 5 or 6 membered saturated heterocyclic ring containing up to one additional heteroatom selected from N, O and S;

n is an integer from 0 to about 4;

j is an integer from 0 to about 7; and k is an integer from 0 to about 7; or $R_3$ is:

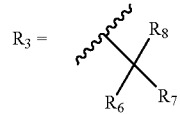

wherein, $R_5$ and $R_7$ are each independently selected from H or alkyl;

$R_8$ is —(CH$_2$)$_j$—C≡C—(CH$_2$)$_k$—R$_9$;

$R_9$ is selected from H, halogen, CN, CF$_3$, N$_3$, COOH, NH$_2$, N(CH$_3$)$_2$, ⊕N(CH$_3$)$_3$, Sn(alkyl)$_3$, phenyl, COOR where R is selected from H or alkyl, a carbocylic ring, a heterocyclic ring, an aromatic ring, a heteroaromatic ring, a polycarbocyclic ring structure having 2 to about 5 rings, a polyheterocyclic ring structure having 2 to about 5 rings or $CONR_{10}R_{11}$ where $R_{10}$ and $R_{11}$ are each independently selected from H, alkyl, hydroxyalkyl or $R_{10}$ and $R_{11}$ together comprise part of a 5 or 6 membered saturated heterocyclic ring containing up to one additional heteroatom selected from N, O and S;

j is an integer from 0 to about 7; and k is an integer from 0 to about 7; or $R_1$ is independently selected from H, OH, alkyl or alkoxy; and $R_3$ is:

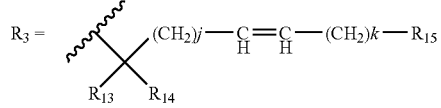

wherein $R_{13}$ and $R_{14}$ are each independently selected from H or alkyl;

$R_{15}$ is selected from halogen, CN, CF$_3$, N$_3$, COOH, NH$_2$, N(CH$_3$)$_2$, ⊕N(CH$_3$)$_3$, Sn(alkyl)$_3$, phenyl, COOR where R is selected from H or alkyl, a carbocylic ring, a heterocyclic ring, an aromatic ring, a heteroaromatic ring, a polycarbocyclic ring structure having 2 to about 5 rings, a polyheterocyclic ring structure having 2 to about 5 rings or $CONR_{10}R_{11}$ where $R_{10}$ and $R_{11}$ are each independently selected from H, alkyl, hydroxyalkyl or $R_{10}$ and $R_{11}$ together comprise part of a 5 or 6 membered saturated heterocyclic ring containing up to one additional heteroatom selected from N, O and S;

j is an integer from 0 to about 7; and k is an integer from 0 to about 7; or

X is >CH—(CH$_2$)$_h$—X$_6$;

$X_6$ is independently selected from I, CN, N$_3$ or COOH and h is an integer from about 1 to about 3, or $X_6$ is selected from I, N$_3$ or COOH and h is an integer from 0 to about 3, including all isomers;

$R_1$ is independently selected from H, OH, alkyl or alkoxy; and $R_3$ is:

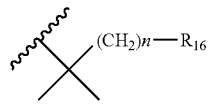

wherein $R_{16}$ is selected from H, halogen, CN, CF$_3$, N$_3$, COOH, NH$_2$, N(CH$_3$)$_2$, ⊕N(CH$_3$)$_3$, Sn(alkyl)

$_3$, phenyl, COOR where R is selected from H or alkyl, a carbocylic ring, a heterocyclic ring, an aromatic ring, a heteroaromatic ring, a polycarbocyclic ring structure having 2 to about 5 rings, a polyheterocyclic ring structure having 2 to about 5 rings or CONR$_{10}$R$_{11}$ where R$_{10}$ and R$_{11}$ are each independently selected from H, alkyl, hydroxyalkyl or R$_{10}$ and R$_{11}$ together comprise part of a 5 or 6 membered saturated heterocyclic ring containing up to one additional heteroatom selected from N, O and S; and n is an integer from 0 to about 7; with the provisos that, X can not be >CH—N$_3$ when R$_1$ is OH and R$_3$ is

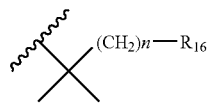

wherein R$_{16}$ is I and n is 6; and

X$_6$ can not be I or COOH when X is >CH—(CH$_2$)$_h$—X$_6$ and R$_3$ is,

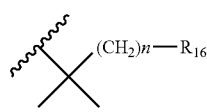

wherein R$_{16}$ is H; and if X is —C=O and R$_1$ is OH and R$_3$ is

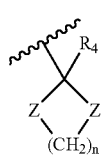

wherein each Z is CH$_3$, than R$_4$ can not be H.

7. The compound of claim 6,
wherein R$_3$ is:

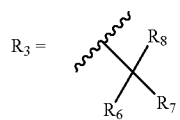

wherein, R$_6$ and R$_7$ are each independently selected from H or alkyl;

R$_8$ is —(CH$_2$)$_j$—C≡C—(CH$_2$)$_k$—R$_9$;

R$_9$ is selected from H, halogen, CN, CF$_3$, N$_3$, COOH, NH$_2$, N(CH$_3$)$_2$, ⊕N(CH$_3$)$_3$, Sn(alkyl)$_3$, phenyl, COOR where R is selected from H or alkyl, a polycarbocyclic ring, a heterocyclic ring, an aromatic ring, a heteroaromatic ring, a polycarbocyclic ring structure having 2 to about 5 rings, a polyheterocyclic ring structure having 2 to about 5 rings or CONR$_{10}$R$_{11}$ where R$_{10}$ and R$_{11}$ are each independently selected from H, alkyl, hydroxyalkyl or R$_{10}$ and R$_{11}$ together comprise part of a 5 or 6 membered saturated heterocyclic ring containing up to one additional heteroatom selected from N, O and S; and j is an integer from 0 to about 7; and k is an integer from 0 to about 7.

8. The compound of claim 6,

R$_1$ is independently selected from H, OH, alkyl or alkoxy; and

R$_3$ is:

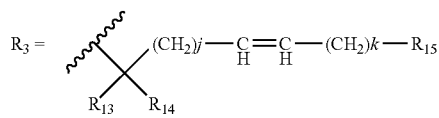

wherein R$_{13}$ and R$_{14}$ are each independently selected from H or alkyl;

R$_{15}$ is selected from halogen, CN, CF$_3$, N$_3$, COOH, NH$_2$, N(CH$_3$)$_2$, ⊕N(CH$_3$)$_3$, Sn(alkyl)$_3$, phenyl, COOR where R is selected from H or alkyl, carbocylic ring, a heterocyclic ring, an aromatic ring, a heteroaromatic ring, a polycarbocyclic ring structure having 2 to about 5 rings, a polyheterocyclic ring structure having 2 to about 5 rings or CONR$_{10}$R$_{11}$ where R$_{10}$ and R$_{11}$ are each independently selected from H, alkyl, hydroxyalkyl or R$_{10}$ and R$_{11}$ together comprise part of a 5 or 6 membered saturated heterocyclic ring containing up to one additional heteroatom selected from N, O and S;

j is an integer from 0 to about 7; and k is an integer from 0 to about 7.

9. The compound of claim 6 wherein:

X is >CH—(CH$_2$)$_h$—X$_6$;

X$_6$ is independently selected from I, CN, N$_3$ or COOH and h is an integer from about 1 to about 3, or X$_6$ is selected from I, N$_3$ or COOH and h is an integer from 0 to about 3, including all isomers;

R$_1$ is independently selected from H, OH, alkyl or alkoxy; and

R$_3$ is:

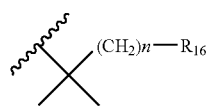

wherein R$_{16}$ is selected from H, halogen, CN, CF$_3$, N$_3$, COOH, NH$_2$, N(CH$_3$)$_2$, ⊕N(CH$_3$)$_3$, Sn(alkyl)$_3$, phenyl, COOR where R is selected from H or alkyl, a carbocylic ring, a heterocyclic ring, an aromatic ring, a heteroaromatic ring, a polycarbocyclic ring structure having 2 to about 5 rings, a polyheterocyclic ring structure having 2 to about 5 rings or CONR$_{10}$R$_{11}$ where R$_{10}$ and R$_{11}$ are each independently selected from H, alkyl, hydroxyalkyl or R$_{10}$ and R$_{11}$ together comprise part of a 5 or 6 membered saturated heterocyclic ring containing up to one additional heteroatom selected from N, O and S; and n is an integer from 0 to about 7.

10. A pharmaceutical composition containing a therapeutically effective amount of at least one of the compounds of claim 1 and physiologically acceptable salts thereof.

11. A method of stimulating cannabinoid receptors in an individual or animal comprising administering to the individual or animal a therapeutically effective amount of at least one of the compounds of claim 1 and physiologically acceptable salts thereof.

12. A method of selectively stimulating CB2 cannabinoid receptors in an individual or animal comprising administering to the individual or animal a therapeutically effective amount of at least one of the compounds of claim 1 and physiologically acceptable salts thereof.

13. The compound of claim 6, wherein $R_3$ is

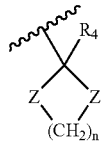

wherein each Z is independently selected from S, O, NH, $N(CH_3)$, SO, $SO_2$ or $CR_{12}R_{13}$ where $R_{12}$ and $R_{13}$ are each independently selected from H or alkyl;

$R_4$ is selected from $-(CH_2)_j-R_5$, $-(CH_2)_j-A-(CH_2)_k-R_5$ or $-(CH_2)_j-A-(CH_2)_k-B-R_5$, A and B are each independently selected from $-CH_2-CH_2-$, $-CH=CH-$, $-C\equiv C-$, O, S, SO, $SO_2$ or NH;

$R_5$ is selected from H, halogen, CN, $CF_3$, $N_3$, COOH, $NH_2$, $N(CH_3)_2$, $\oplus N(CH_3)_3$, $Sn(alkyl)_3$, phenyl, COOR where R is selected from H or alkyl, a carbocylic ring, a heterocyclic ring, an aromatic ring, a heteroaromatic ring, a polycarbocyclic ring structure having 2 to about 5 rings, a polyheterocyclic ring structure having 2 to about 5 rings or $CONR_{10}R_{11}$ where $R_{10}$ and $R_{11}$ are each independently selected from H, alkyl, hydroxyalkyl or $R_{10}$ and $R_{11}$ together comprise part of a 5 or 6 membered saturated heterocyclic ring containing up to one additional heteroatom selected from N, O and S;

n is an integer from 1 to about 4;

j is an integer from 0 to about 7; and k is an integer from 0 to about 7.

14. A pharmaceutical composition containing a therapeutically effective amount of at least one of the compound of claim 6 and physiologically acceptable salts thereof.

15. A method of stimulating cannabinoid receptors in an individual or animal comprising administering to the individual or animal a therapeutically effective amount of at least one of the compounds of claim 6 and physiologically acceptable salts thereof.

16. The method of claim 15 wherein the compound more selectively binds to the CB2 cannabinoid receptors in the individual or animal.

* * * * *

UNITED STATES PATENT AND TRADEMARK OFFICE
CERTIFICATE OF CORRECTION

PATENT NO.      : 7,057,076 B2
APPLICATION NO. : 10/483482
DATED           : June 6, 2006
INVENTOR(S)     : Makriyannis et al.

It is certified that error appears in the above-identified patent and that said Letters Patent is hereby corrected as shown below:

Column 29:

Lines 41 – 51, delete:                              and substitute:

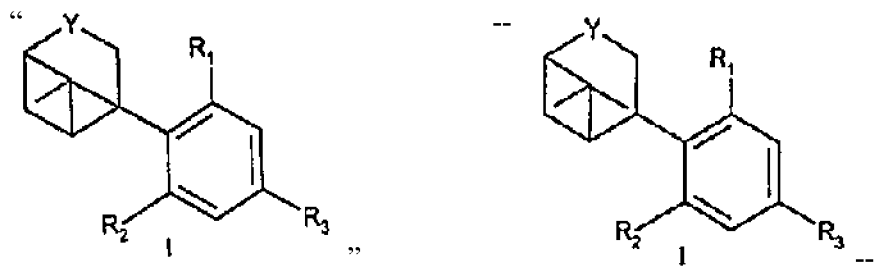

Column 30:

Line 17, after "part" delete "at" and substitute --of--.

Column 31:

Line 18, delete "$R_5$" and substitute --$R_6$--.

Line 64, delete "$Y_5$" and substitute --$Y_6$--.

Column 32:

Line 9, delete "$\oplus N(CH_{3)3}$" and substitute --$\oplus N(CH_3)_3$--.

Line 21, delete "$NH_2$" and substitute --$NH_2$,--.

Line 22, delete "and".

Line 22, after "1 – 3," insert --and 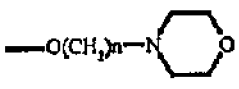 where n is an integer between 1-3,--

UNITED STATES PATENT AND TRADEMARK OFFICE
CERTIFICATE OF CORRECTION

PATENT NO. : 7,057,076 B2
APPLICATION NO. : 10/483482
DATED : June 6, 2006
INVENTOR(S) : Makriyannis et al.

It is certified that error appears in the above-identified patent and that said Letters Patent is hereby corrected as shown below:

Column 33:

Line 66, after "$R_2$" delete "each independently comprise" and substitute --are each independently selected from--.

Column 34:

Line 8, after "wherein" delete "$R_{15}$" and substitute --$R_{16}$--.

Lines 24 – 32, delete
" 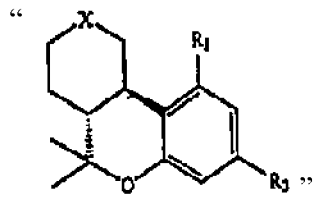 and substitute -- 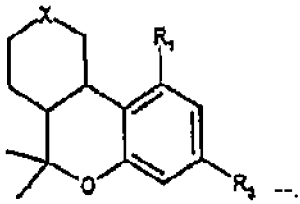 --.

Column 35:

Line 26, before "each" insert --are--.

Line 41, after "Z" insert --is--.

Line 47, after "B" insert --are--.

Line 64, delete "0 to about 4;" and substitute --1 to about 4;--.

Column 36:

Line 9, after "wherein" delete "$R_5$" and substitute --$R_6$--.

Line 67, delete "Sn(alkyl)" and substitute --$Sn(alkyl)_3$,--.

Column 37:

Line 1, before "phenyl" delete "$_3$,".

UNITED STATES PATENT AND TRADEMARK OFFICE
CERTIFICATE OF CORRECTION

PATENT NO. : 7,057,076 B2  Page 3 of 3
APPLICATION NO. : 10/483482
DATED : June 6, 2006
INVENTOR(S) : Makriyannis et al.

It is certified that error appears in the above-identified patent and that said Letters Patent is hereby corrected as shown below:

Column 37:

Line 40, after "than $R_4$ can not be H" insert --and if R, is OH, and X is > $CH_2$, > CHOH, > $CHOCH_3$, $CHOCH_2CH_3$, > CHhalogen, > CHCN, > $CHCH_3$, > $CHCF_3$, > $CHCH_2OH$, > $CHCH_2OCH_3$, > $CHCH_2OCH_2CH_3$, > $CHCH_2$(halogen), > $CHCH_2CN$, > $CHCH_2CH_3$, > $CHCH_2CF_3$, > $CHCH_2NH_2$, > $CHCH_2NHCH_3$ or > $CHCH_2N(CH_3)_2$, than R3 cannot be a carbocyclic ring, a heterocyclic ring, or any above group substituted with one or more members selected from the group consisting of -H, -OH, $-OCH_3$, $-OCH_2CH_3$, halogen, -CN, $-N_3$, -NCO, -NCS, $-NO_2$, $-CH_3$, -C(halogen)$_3$, $-CH_2OH$, $-CH_2OCH_3$, $-CH_2OCH_2CH_3$, $-CH_2$(halogen), $-CH_2CN$, $-CH_2NO_2$, $-CH_2CH_3$, $-CH_2C$(halogen)$_3$, $-CH_2NH_2$, $-CH_2NHCH_3$ and $-CH_2N(CH_3)_2$--.

Line 57, delete "polycarbocyclic" and substitute --carbocyclic--.

Column 38:

Line 16, before "carbocyclic" insert --a--.

Column 40:

Line 13, delete "compound" and substitute --compounds--.

Signed and Sealed this

Sixth Day of March, 2007

JON W. DUDAS
*Director of the United States Patent and Trademark Office*